(12) United States Patent
Yen et al.

(10) Patent No.: US 11,084,786 B2
(45) Date of Patent: Aug. 10, 2021

(54) COMPOUNDS AND PHARMACEUTICAL COMPOSITION ASSOCIATED WITH UBIQUITINATION-PROTEASOME SYSTEM

(71) Applicant: CALGENT BIOTECHNOLOGY CO., LTD., Taipei (TW)

(72) Inventors: Yun Yen, Arcadia, CA (US); Jing-Ping Liou, Taipei (TW); Shiow-Lin Pan, Taipei (TW)

(73) Assignee: CALGENT BIOTECHNOLOGY CO., LTD., Taipei (TW)

( * ) Notice: Subject to any disclaimer, the term of this patent is extended or adjusted under 35 U.S.C. 154(b) by 0 days.

(21) Appl. No.: 16/907,084

(22) Filed: Jun. 19, 2020

(65) Prior Publication Data
US 2020/0385344 A1    Dec. 10, 2020

Related U.S. Application Data

(62) Division of application No. 15/748,827, filed as application No. PCT/US2016/044932 on Jul. 30, 2016, now Pat. No. 10,745,350.

(60) Provisional application No. 62/199,207, filed on Jul. 30, 2015.

(51) Int. Cl.

| | | |
|---|---|---|
| *A61K 31/40* | (2006.01) |
| *A61K 31/166* | (2006.01) |
| *A61K 31/122* | (2006.01) |
| *C07D 207/04* | (2006.01) |
| *A61K 45/06* | (2006.01) |
| *A61P 35/00* | (2006.01) |
| *C07D 295/135* | (2006.01) |
| *C07D 295/13* | (2006.01) |
| *C07C 311/29* | (2006.01) |
| *C07C 237/34* | (2006.01) |
| *C07D 213/40* | (2006.01) |
| *C07C 225/30* | (2006.01) |
| *C07C 255/58* | (2006.01) |
| *C07D 209/08* | (2006.01) |
| *C07D 209/44* | (2006.01) |
| *C07D 215/38* | (2006.01) |
| *C07D 215/40* | (2006.01) |
| *A61K 31/7048* | (2006.01) |
| *C07C 235/54* | (2006.01) |
| *A61K 33/243* | (2019.01) |
| *A61P 25/14* | (2006.01) |
| *A61P 25/28* | (2006.01) |
| *A61P 3/10* | (2006.01) |
| *C07C 237/48* | (2006.01) |

(52) U.S. Cl.
CPC .......... *C07D 207/04* (2013.01); *A61K 31/122* (2013.01); *A61K 31/166* (2013.01); *A61K 31/40* (2013.01); *A61K 31/7048* (2013.01); *A61K 33/243* (2019.01); *A61K 45/06* (2013.01); *A61P 3/10* (2018.01); *A61P 25/14* (2018.01); *A61P 25/28* (2018.01); *A61P 35/00* (2018.01); *C07C 225/30* (2013.01); *C07C 235/54* (2013.01); *C07C 237/34* (2013.01); *C07C 237/48* (2013.01); *C07C 255/58* (2013.01); *C07C 311/29* (2013.01); *C07D 209/08* (2013.01); *C07D 209/44* (2013.01); *C07D 213/40* (2013.01); *C07D 215/38* (2013.01); *C07D 215/40* (2013.01); *C07D 295/13* (2013.01); *C07D 295/135* (2013.01); *C07C 2602/10* (2017.05)

(58) Field of Classification Search
None
See application file for complete search history.

(56) References Cited

FOREIGN PATENT DOCUMENTS

WO     WO 2014201016    *   6/2014    ............. A61K 31/54

* cited by examiner

*Primary Examiner* — Samantha L Shterengarts
(74) *Attorney, Agent, or Firm* — Prosyla Group PC

(57) ABSTRACT

The invention relates to new compounds with low cytotoxicity for blocking ubiquitination-proteasome system in diseases. Accordingly, these compounds can be used in treatment of treating disorders including, but not limited to, cancers, neurodegenerative diseases, inflammatory disorders and autoimmune disorders and metabolic disorders.

12 Claims, 1 Drawing Sheet

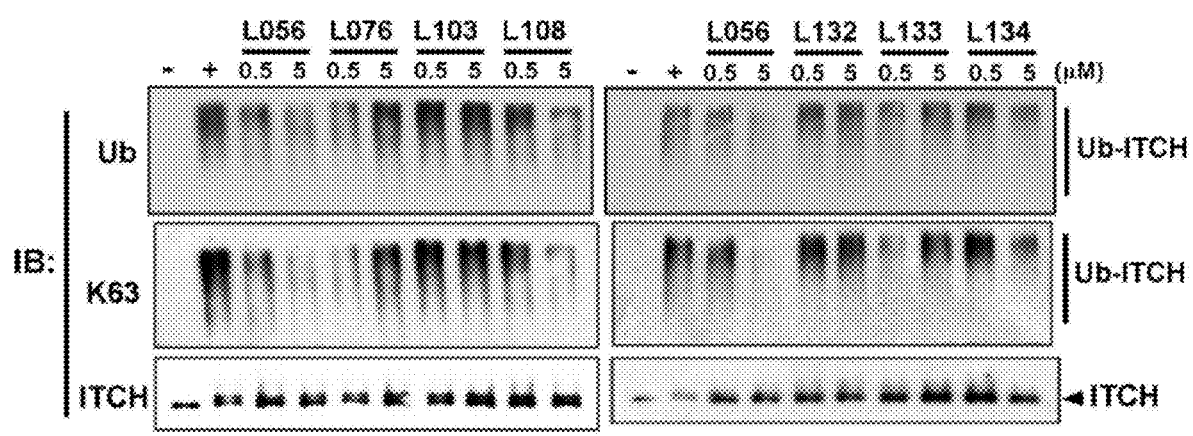

COMPOUNDS AND PHARMACEUTICAL COMPOSITION ASSOCIATED WITH UBIQUITINATION-PROTEASOME SYSTEM

RELATED APPLICATIONS

This application claims the benefit and priority to U.S. patent application Ser. No. 15/748,827, filed on Jan. 30, 2018, entitled, "COMPOUNDS AND PHARMACEUTICAL COMPOSITION ASSOCIATED WITH UBIQUITINATION-PROTEASOME SYSTEM", which is a National Phase 371 Application of International Patent Application No. PCT/US16/44932, filed Jul. 30, 2016, which claims the benefit and priority to U.S. Provisional Patent Application No. 62/199,207, filed Jul. 30, 2015, the contents of which are incorporated by reference herewith in their entirety.

FIELD OF THE INVENTION

The present invention relates to the identification of new drug targets for therapy of disorders. In particular, the present invention relates to new drug targets with low cytotoxicity for blocking the ubiquitination-proteasome system in diseases.

BACKGROUND OF THE INVENTION

Cancer is a disease in which cells in the body grow out of control. The majority of the current cancer treatment methods result in severe general toxicity to the human body. Both radiation and chemotherapy have deleterious effects to the host, causing significant morbidity and mortality. Hence, there is a need in the art for non-invasive and non-toxic methods of treating cancer and preventing tumor growth. However, the cancer cannot be effectively cured. Therefore, there is a need to develop a compound effectively treating a cancer but having low cytotoxicity.

Inflammation is a mechanism that protects mammals from invading pathogens. However, while transient inflammation is necessary to protect a mammal from infection, uncontrolled inflammation causes tissue damage and is the underlying cause of many illnesses. Inflammation is typically initiated by binding of an antigen to T-cell antigen receptor. Antigen binding by a T-cell initiates calcium influx into the cell via calcium ion channels, such as $Ca^{2+}$-release-activated $Ca^{2+}$ channels (CRAC). Calcium ion influx in turn initiates a signaling cascade that leads to activation of these cells and an inflammatory response characterized by cytokine production. Over production of proinflammatory cytokines other than IL-2 has also been implicated in many autoimmune diseases. Therefore, there is a continuing need for new drugs which overcome one or more of the shortcomings of drugs currently used for the treatment or prevention of inflammatory disorders, allergic disorders and autoimmune disorders.

Proteasomes are part of a major mechanism by which cells regulate the concentration of particular proteins and degrade misfolded proteins. Proteasomes are large ring- or cylinder-shaped multicomponent complexes common to all eukaryotic cells. Proteasomes are large multi-subunit protease complexes, localized in the nucleus and cytosol, which selectively degrade intracellular proteins. Proteasomes play a major role in the degradation of many proteins that are involved in cell cycling, proliferation, and apoptosis. They have at least three distinct endopeptidase activities which include hydrolysis of peptide bonds on the carboxyl side of hydrophobic, basic, and acidic amino acid residues. Proteasomes, through their protein degradation activity, have been implicated in several important cell functions, including DNA repair, cell cycle progression, signal transduction, transcription, and antigen presentation.

Proteasome inhibition represents an important new strategy in cancer treatment.

U.S. Pat. Nos. 7,442,830, 8,003,819 and 8,058,262 relate to boronic acid and boronic ester compounds useful as proteasome inhibitors. U.S. Pat. No. 8,389,564 provides salinosporamide used to treating and/or ameliorating a disease or condition, such as cancer, a microbial disease and/or inflammation. WO 2010/005534 provides compounds having activity as inhibitors of proteasomes.

However, there is an ongoing need for new and/or improved inhibitors of proteasome.

SUMMARY OF THE INVENTION

One aspect of the invention is to provide a compound having the following Formula (I):

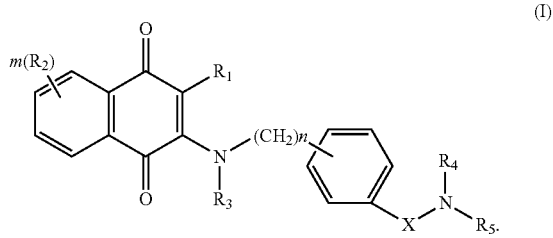

Another aspect of the invention is to provide a compounds having the following Formula (II):

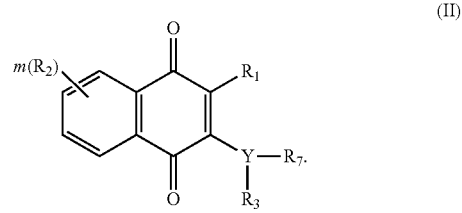

Another aspect of the invention is to provide a pharmaceutical composition containing a compound of Formula (I) or Formula (II).

A further aspect is to provide a method for inhibiting ITCH E3 ligase, comprising administrating a compound of Formula (I) or Formula (II) to a cell or a subject.

Another further aspect is to provide a method for treating a cancer, comprising administrating a compound of Formula (I) or Formula (II) to a cell or a subject.

Another further aspect is to provide a method for treating autoimmune disorders, comprising administrating a compound of Formula (I) or Formula (II) to a cell or a subject.

BRIEF DESCRIPTION OF THE DRAWINGS

FIG. 1 shows the compounds of the invention block ITCH self-ubiquitnation (Lys-dependent) more efficiently than the control compound.

DETAILED DESCRIPTION OF THE INVENTION

The invention relates to new compounds with low cytotoxicity for blocking the ubiquitination-proteasome system in diseases. Accordingly, these compounds can be used to treat disorders including, but not limited to, cancers, inflammatory disorders and autoimmune disorders.

Definitions and Terms

Terms not specifically defined herein should be understood according to the meanings that would be given to them by one of skill in the art in light of the disclosure and the context. As used in the specification, however, unless specified to the contrary, the following terms have the meaning indicated according to the following conventions.

The terms "a" and "an" refer to one or more.

The terms "disease" and "disorder" herein can be used interchangeably.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compounds, compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

The term "pharmaceutically acceptable" is employed herein to refer to those compounds, materials, compositions, and/or dosage forms which are, within the scope of medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines, pyridine, pyrimidine and quinazoline; alkali or organic salts of acidic residues such as carboxylic acids; and the like.

As used herein, the term "stereoisomer" is a general term for all isomers of individual molecules that differ only in the orientation of their atoms in space. It includes enantiomers and isomers of compounds with more than one chiral center that are not mirror images of one another (diastereoisomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers that is optically inactive.

The term "resolution" refers to the separation or concentration or depletion of one of the two enantiomeric forms of a molecule.

As used herein, halo or halogen refers to fluoro, chloro, bromo or iodo.

As used herein, the term "alkyl" refers to straight or branched hydrocarbon chains containing the specified number of carbon atoms. For example, "$C_1$-$C_6$ alkyl" is selected from straight-chained and branched non-cyclic hydrocarbons having from 1 to 6 carbon atoms. Representative straight chain $C_1$-$C_6$ alkyl groups include -methyl, -ethyl, -n-propyl, -n-butyl, -n-pentyl, and -n-hexyl. Representative branched $C_1$-$C_6$ alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

As used herein, the term "alkenyl" refers to straight or branched chain hydrocarbon chains containing the specified number of carbon atoms and one or more double bonds. For example, "$C_2$-$C_6$ alkenyl" is selected from straight chain and branched non-cyclic hydrocarbons having from 2 to 6 carbon atoms and including at least one carbon-carbon double bond. Representative straight chain and branched $C_2$-$C_6$ alkenyl groups include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, 2-hexenyl, and 3-hexenyl.

As used herein, a "$C_2$-$C_6$ alkynyl" is selected from straight chain and branched non-cyclic hydrocarbon having from 2 to 6 carbon atoms and including at least one carbon-carbon triple bond. Representative straight chain and branched $C_2$-$C_6$ alkynyl groups include -acetylenyl, -propynyl, -1-butyryl, -2-butyryl, -1-pentynyl, -2-pentynyl, -3-methyl-1-butynyl, -4-pentynyl, -1-hexynyl, -2-hexynyl, and -5-hexynyl.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —($CH_2$)—, —($CH_2$—$CH_2$)—, —(CH($CH_3$))—, —($CH_2$—$CH_2$—$CH_2$)—, —(C($CH_3$)$_2$)—, —(CH($CH_2CH_3$))—, —(CH($CH_3$)—$CH_2$)—, —($CH_2$—CH($CH_3$))—, —($CH_2$—$CH_2$—$CH_2$—$CH_2$)—, —($CH_2$—$CH_2$—CH($CH_3$))—, —(CH($CH_3$)—$CH_2$—$CH_2$)—, —($CH_2$—CH($CH_3$)—$CH_2$)—, —($CH_2$—C($CH_3$)$_2$)—, —(C($CH_3$)$_2$—$CH_2$)—, —(CH($CH_3$)—CH($CH_3$))—, —($CH_2$—CH($CH_2CH_3$))—, —(CH($CH_2CH_3$)—$CH_2$)—, —(CH($CH_2CH_2CH_3$))—, —(CHCH($CH_3$)$_2$)— and —C($CH_3$)($CH_2CH_3$)—.

As used herein, "cycloalkyl" refers to a group selected from $C_3$-$C_{12}$ cycloalkyl, and preferably a $C_{3-8}$ cycloalkyl.

Typical cycloalkyl groups include cyclopropyl, cyclobutyl, cyclopentyl, cyclohexyl, cycloheptyl, cyclooctyl, and cyclononyl.

As used herein, the term "heterocyclyl" refers to groups containing one to four heteroatoms each selected from O, S and N, wherein each heterocyclic group has from 4 to 10 atoms in its ring system, and wherein the ring of said group does not contain two adjacent O or S atoms. Typical heterocyclyl groups include pyrrolidinyl, tetrahydrofuranyl, dihydrofuranyl, tetrahydrothienyl, tetrahydropyranyl, dihydropyranyl, tetrahydrothiopyranyl, piperidino, sulfolanyl, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroquinazolinyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl.

As used herein, the term "alkoxy" refers to a straight or branched alkoxy group containing the specified number of carbon atoms. For example, $C_{1-6}$alkoxy means a straight or branched alkoxy group containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy. The point of attachment may be on the oxygen or carbon atom.

As used herein, the term "alkylthio (also termed as alkylsulfanyl) refers to straight-chain or branched alkyl groups (preferably having 1 to 6 carbon atoms, e.g. 1 to 4 carbon atoms ($C_1$-$C_6$-alkylthio), which are bound to the remainder of the molecule via a sulfur atom at any bond in the alkyl group. Examples of $C_1$-$C_4$-alkylthio include methylthio, ethylthio, n-propylthio, isopropylthio, n-butylthio, sec-butylthio, isobutylthio and tert-butylthio. Examples of $C_1$-$C_6$-alkylthio include, apart from those mentioned for $C_1$-$C_4$-alkylthio, 1-, 2- and 3-pentylthio, 1-, 2- and 3-hexylthio and the positional isomers thereof.

As used herein, the term "alkoxyalkyl" refers to the group -alk$_1$-O-alk$_2$ where alk$_1$ is alkyl or alkenyl, and alk$_2$ is alkyl or alkenyl.

As used herein, the term "alkylamino" refers to the group —NRR' where R is alkyl and R' is hydrogen or alkyl.

As used herein, "aryl" refers to a group selected from $C_{6-14}$ aryl, especially $C_{6-10}$ aryl. Typical $C_{6-14}$ aryl groups include phenyl, naphthyl, phenanthryl, anthracyl, indenyl, azulenyl, biphenyl, biphenylenyl and fluorenyl groups.

As used herein, "heteroaryl" refers to a group having from 5 to 14 ring atoms; 6, 10 or 14 pi electrons shared in a cyclic array; and containing carbon atoms and 1, 2 or 3 oxygen, nitrogen and/or sulfur heteroatoms. Examples of heteroaryl groups include indazolyl, furyl, thienyl, pyrrolyl, imidazolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, tetrazolyl, triazinyl, azepinyl, oxazepinyl, morpholinyl, thiazepinyl, diazepinyl, thiazolinyl, benzimidazolyl, benzoxazolyl, imidazopyridinyl, benzoxazinyl, benzothiazinyl, benzothiophenyl oxazolopyridinyl, benzofuranyl, quinolinyl, quinazolinyl, quinoxalinyl, benzothiazolyl, phthalimido, benzofuranyl, benzodiazepinyl, indolyl, indanyl, azaindazolyl, deazapurinyl and isoindolyl.

As used herein, the term "amino" or "amino group" refers to —NH$_2$.

As used herein, the term "optionally substituted" refers to a group that is unsubstituted or substituted with one or more substituents. For example, where the groups $C_1$-$C_6$ alkyl, $C_2$-$C_6$ alkenyl, $C_2$-$C_6$ alkynyl, —O—$C_1$-$C_6$ alkyl, —O—$C_2$-$C_6$ alkenyl, and —O—$C_2$-$C_5$ alkynyl are referred to as being optionally substituted, they may or may not be substituted. Where substituted, they may be substituted with a group selected from the group consisting of halo, halo($C_{1-6}$)alkyl, (halo)$_2$($C_{1-6}$)alkyl, (halo)$_3$($C_{1-6}$)alkyl, aryl, heteroaryl, cycloalkyl, heterocycloalkyl, $C_{1-6}$ alkyl, $C_{2-6}$ alkenyl, $C_{2-6}$ alkynyl, aryl($C_{1-6}$)alkyl, aryl($C_{2-6}$)alkenyl, aryl($C_{2-6}$)alkynyl, cycloalkyl($C_{1-6}$)alkyl, heterocyclo($C_{1-6}$)alkyl, hydroxyl ($C_{1-6}$)alkyl, amino($C_{1-6}$)alkyl, carboxy($C_{1-6}$)alkyl, alkoxy ($C_{1-6}$)alkyl, nitro, amino, ureido, cyano, alkylcarbonylamino, hydroxyl, thiol, alkylcarbonyloxy, azido, alkoxy, carboxy, aminocarbonyl, and $C_{1-6}$alkylthiol. Preferred optional substituents include halo, halo($C_{1-6}$)alkyl, (halo)$_2$($C_{1-6}$)alkyl, (halo)$_3$($C_{1-6}$)alkyl, hydroxyl($C_{1-6}$)alkyl, amino($C_{1-6}$)alkyl, hydroxyl, nitro, $C_{1-6}$alkyl, C1-6alkoxy and amino. Preferred numbers of optional substituents are 1, 2 or 3.

Compounds of the Invention or a Tautomer or Stereoisomer Thereof, or a Solvate, Prodrug or a Pharmaceutically Acceptable Salt Thereof In one aspect, the invention provides a compound having the following Formula (I):

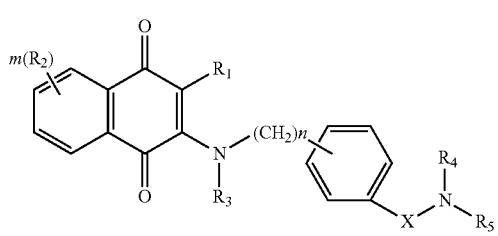

wherein $R_1$ is halogen, alkyl, alkenyl, alkynyl, NH$_2$, NO$_2$, OH or CN; each $R_2$ is the same or different, representing H, alkyl, $C_{2-10}$alkenyl, alkynyl, NH$_2$, NO$_2$, $C_{1-10}$alkyloxy, alkylthio, alkylamino, alkyloxyalkyl, OH or CN, aryl or heterocyclic having 1 to 3 heteroatoms selected from the group consisting of N, O and S;

$R_3$ is H, alkyl, alkenyl, alkynyl, NH$_2$, NO$_2$, OH or CN;

$R_4$ is H, alkyl, alkenyl, alkynyl, NH$_2$, NO$_2$, OH or CN, or $R_4$ together with nitrogen atom attached therefrom and $R_5$ form a fused bicyclic ring having 0 to 3 heteroatoms selected from O; N and S;

$R_5$ is alkylene-$R_6$ wherein $R_6$ is OH, NO$_2$, CN, alkyl, alkenyl, alkynyl, NR$_a$R$_b$, cycloalkyl, aryl, heterocyclic ring having 0 to 3 heteroatoms selected from O; N and S or fused heterocyclic ring having 0 to 3 hetero atoms selected from O, N and S, each of cycloalkyl, aryl, heterocyclic ring and fused heterocyclic ring is unsubstituted or substituted with one to three of OH; halogen; NH$_2$; NO$_2$, CN, alkyl; alkenyl; alkynyl; alkyloxy; heteroaryl having 1 to 3 heteroatoms selected from the group consisting of N, O and S, unsubstituted or substituted with alkyl, alkenyl, alkynyl, OH, halogen, CN, NH$_2$ or NO$_2$; and $R_a$ and $R_b$ are the same or different, independently representing H; OH; alkyl; alkenyl; alkynyl; alkyloxy; cycloalkyl; heterocyclyl; alkyleneamino; alkylene-N-(alkyl)$_2$; aryl unsubstituted or substituted with OH, halogen, CN, NH$_2$, NO$_2$, alkyl, alkenyl, alkynyl, alkyloxy or heteroaryl; heteroaryl unsubstituted or substituted with OH, halogen, CN, NH$_2$, NO$_2$, alkyl, alkenyl, alkynyl or alkyloxy; alkylene-heteroaryl; or alkylene-heterocylyl unsubstituted or substituted with alkyl;

X is —C(O), —S(O)$_2$ or —NH—C(O)—;

m is an integer of 0-3; and n is an integer of 0-7;

or a tautomer or stereoisomer thereof, or a solvate, prodrug or a pharmaceutically acceptable salt thereof.

In some embodiments of formula (I), m is 0; R$_1$ is halogen; n is any integer of 1-4; R$_3$ is H; X is C(O); R$_4$ is H; R$_5$ is alkylene-R$_6$ wherein R$_6$ is NR$_a$R$_b$, C$_{5-7}$heterocyclic ring having 0 to 3 hetero atoms selected from O, N and S; or C$_{10-12}$ fused heterocyclic ring having 0 to 3 hetero atoms selected from O, N and S; and R$_a$ and R$_b$ are alkyl.

In some embodiments of formula (I), m is 0; R$_1$ is halogen; n is any integer of 1-2; R$_3$ is H; X is C(O); R$_4$ is H; R$_5$ is (CH$_2$)$_{1-4}$R$_6$ wherein R$_6$ is unsubstituted or substituted pyrrolidinyl, oxolanyl, thiolanyl, pyrrolyl, furanyl, thiophenyl, piperidinyl, oxanyl, thianyl, morpholinoyl, pyridinyl, piperidinyl, piperazinyl, thiopyranyl, pyrazinyl, pyrimidinyl, pyridazinyl, thiazolyl; benzimidazolyl; pyrazolyl; indazolyl; pyrazolyl; quinolinyl; indolyl; indazolyl; azaindolyl; azaindazolyl; deazapurinyl; or indanyl.

In some embodiments of formula (I), m is 0; R$_1$ is halogen; n is any integer of 1-2; R$_3$ is H; X is C(O); R$_4$ is H; R$_5$ is (CH$_2$)$_{1-4}$R$_6$ wherein R$_6$ is unsubstituted or substituted pyrrolidinyl, morpholinoyl, pyridinyl, piperidinyl, piperazinyl, or indolyl.

In some embodiments of formula (I), m is 0; R$_1$ is Cl; n is 1; R$_3$ is H, x is C(O); R$_4$ is H R$_5$ is CH$_2$CH$_2$N(CH$_3$)$_2$, pyrrolidinyl substituted by ethyl, or CH$_2$N(CH$_2$CH$_3$)$_2$.

In some embodiments formula (I), the compounds include but not limited to the following:

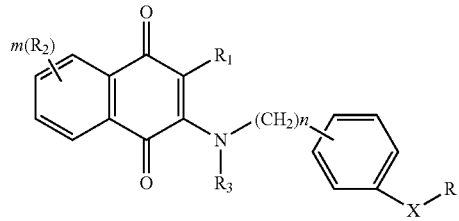

m is 0; R$_3$ is H; X is C(O); and R is

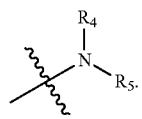

| Example (Compound #) | Code | Number | R$_1$ | (CH$_2$)$_n$ | Structure of R |
|---|---|---|---|---|---|
| Example 25 (27) | MPT0L102 | 19-1717 | Cl | CH$_2$ | *N-CH$_2$-pyridin-4-yl* |
| Example 41 (43) | MPT0L122 | 19-1935 | Cl | CH$_2$ | *N-CH$_2$CH$_2$-morpholinyl* |
| Example 42 (44) | MPT0L123 | 19-1936 | Cl | CH$_2$ | *N-CH$_2$CH$_2$-indol-3-yl* |
| Example 43 (45) | MPT0L132 | | Cl | CH$_2$ | *N-CH$_2$CH$_2$-N(CH$_3$)$_2$* |
| Example 44 (46) | MPT0L133 | | Cl | CH$_2$ | *N-CH$_2$CH$_2$-pyrrolidinyl* |
| Example 45 (47) | MPT0L134 | | Cl | CH$_2$ | *N-CH$_2$CH$_2$-N(CH$_2$CH$_3$)$_2$* |

-continued

| Example (Compound #) | Code | Number R₁ | (CH₂)ₙ | Structure of R |
|---|---|---|---|---|
| Example 46 (48) | MPT0L136 | Cl | CH₂ | |
| Example 47 (49) | MPT0L137 | Cl | CH₂ | |

In some embodiments of formula (I), the compound is selected from the group consisting of:

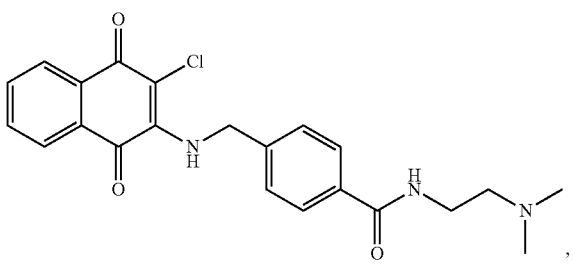

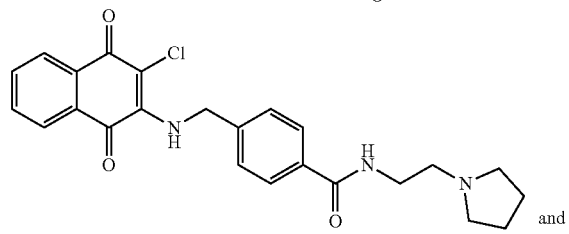

and

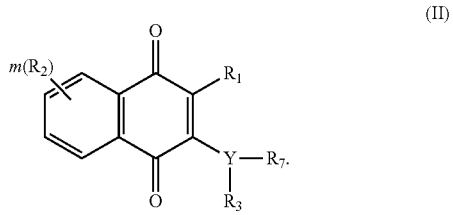

or a tautomer or stereoisomer thereof, or a solvate, prodrug or a pharmaceutically acceptable salt thereof.

In another aspect, the invention provides a compounds having the following Formula (II):

(II)

wherein
Y is —N—, —N—(CH₂)ₙ— or —NC(O)—;
m is an integer of 0-4;

$R_1$ is halogen, $C_{1-10}$alkyl, $C_{2-10}$alkenyl, $C_{2-10}$alkynyl, $NH_2$, $NO_2$, OH or CN;

each $R_2$ is the same or different, representing H, $C_{1-10}$alkyl, $C_{2-10}$alkenyl, $C_{2-10}$alkynyl, $NH_2$, $NO_2$, $C_{1-10}$ alkyloxy, $C_{1-10}$alkylthio, $C_{1-10}$alkylamino, $C_{1-10}$alkyloxy$C_{1-10}$alkyl, OH or CN, $C_{6-10}$ aryl or $C_{5-7}$heterocyclic having 1 to 3 heteroatoms selected from the group consisting of N, O and S;

$R_3$ is H, $C_{1-10}$alkyl, $C_{2-10}$alkenyl, $C_{2-10}$alkynyl, $NH_2$, $NO_2$, OH, CN or $R_3$ together with $R_7$ forms a heterocyclic ring; and $R_7$ is aryl unsubstituted or substituted by one to five of OH, halogen, $NH_2$, $NO_2$, CN, alkyl, alkenyl, alkynyl, alkyloxy, aryl, —NHSO₂aryl wherein aryl is unsubstituted or substituted by alkyloxy, OH, halogen, $NH_2$, $NO_2$, CN, alkyl, alkenyl, alkynyl, alkylthio, alkylamino, alkyloxyalkyl, or heteroaryl unsubstituted or substituted by alkyl, alkenyl, alkynyl, OH, halogen, CN, $NH_2$ or $NO_2$; heterocyclic ring unsubstituted or substituted by alkyloxy, OH, halogen, $NH_2$, $NO_2$, CN, alkyl, alkenyl, alkynyl, alkylthio, alkylamino, alkyloxyalkyl, —SO₂aryl unsubstituted or substituted by alkyloxy, OH, halogen, $NH_2$, $NO_2$, CN, alkyl, alkenyl, alkynyl, alkylthio, alkylamino or alkyloxyalkyl, or —C(O)aryl unsubstituted or substituted by one to five of OH, halogen, $NH_2$, $NO_2$, CN, alkyl, alkenyl, alkynyl, alkyloxy or aryl; or fused heterocyclic ring unsubstituted or substituted by alkyloxy, OH, halogen, $NH_2$, $NO_2$, CN, alkyl, alkenyl, alkynyl, alkylthio, alkylamino, alkyloxyalkyl, —SO₂aryl unsubstituted or substituted by alkyloxy, OH, halogen, $NH_2$, $NO_2$, CN, alkyl, alkenyl, alkynyl, alkylthio, alkylamino or alkyloxyalkyl;

or a tautomer or stereoisomer thereof, or a solvate, prodrug or a pharmaceutically acceptable salt thereof.

In one embodiment of formula (II), m is 0; $R_1$ is halogen; Y is —N—; $R_3$ is H or $C_{1-10}$alkyl; and $R_7$ is phenyl unsubstituted or substituted by one to five halogen, $C_{1-10}$alkyloxy, —N(H)S(O₂)phenyl unsubstituted or substituted by $C_{1-10}$alkyloxy or $C_{1-10}$alkylpiperazinyl; quinolinyl, indolyl or indolinyl unsubstituted or substituted by —S(O₂)phenyl substituted by $C_{1-10}$alkyloxy.

In one embodiment of formula (II), m is 0; $R_1$ is halogen; Y is a bond; and $R_3$ together with $R_7$ forms a isoindolinyl.

In one embodiment of formula (II), m is 0; $R_1$ is halogen; Y is —NC(O)— or —N—(CH₂)₁₋₄; $R_3$ is H; and $R_7$ is phenyl$C_{1-4}$alkoxy or piperazinyl$C_{1-10}$alkyl.

In one embodiment of formula (II), m is 0; $R_1$ is halogen; Y is a —N— or —N—(CH₂)₁₋₄; $R_3$ is H; and $R_7$ is indolinyl substituted by C(O)phenyl substituted by one to four OH or $C_{1-10}$alkyl.

In some embodiments formula (I), the compounds include but not limited to the following:

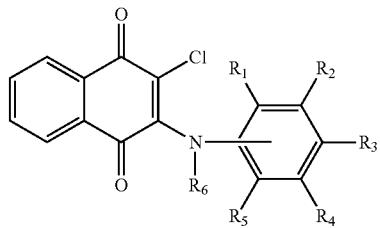

| Example (Compound #) | Code | Number | R6 | R1 | R2 | R3 | R4 | R5 |
|---|---|---|---|---|---|---|---|---|
| Example 92 (71) | MPT0L029 | 21-1062 | H | H | H | NHSO$_2$Ph(p-OCH$_3$) | H | H |
| Example 94 (72) | MPT0L030 | 21-1080 | H | H | NHSO$_2$Ph(p-OCH$_3$) | H | H | H |
| Example 97 (75) | MPT0L045 | 31-184 | C$_2$H$_5$ | H | H | F | H | H |
| Example 98 (76) | MPT0L046 | 31-218 | H | H | H | 4-methylpiperazine-1-yl | H | H |
| Example 99 (77) | MPT0L047 | 31-238 | H | H | H | 4-ethylpiperazine-1-yl | H | H |
| Example 100 (78) | MPT0L048 | 19-1425-2A | H | F | H | I | H | H |
| Example 101 (79) | MPT0L049 | 19-1442 | H | Cl | OCH$_3$ | Cl | OCH$_3$ | Cl |
| Example 102 (80) | MPT0L050 | 19-1444 | H | CN | H | I | H | H |

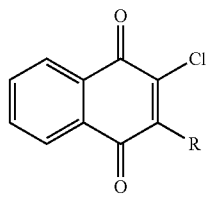

| Example (Compound #) | Code | Number | Structure of R |
|---|---|---|---|
| Example 103 (81) | MPT0L026 | 31-158 | |
| Example 104 (82) | MPT0L027 | 31-160 | |
| Example 105 (83) | MPT0L028 | 31-170 | |
| Example 106 (84) | MPT0L032 | 21-1101 | |

-continued
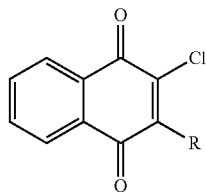
| Example (Compound #) | Code | Number | Structure of R |
|---|---|---|---|
| Example 107 (85) | MPT0L033 | 21-1102 | (5-indolylamino) |
| Example 108 (86) | MPT0L035 | 21-1104B | (1-(4-methoxyphenylsulfonyl)-5-indolinylamino) |
| Example 109 (87) | MPT0L009 | 19-1217 | (1-(4-methoxyphenylsulfonyl)-7-indolinylamino) |
| Example 110 (88) | MPT0L044 | 31-164 | (8-quinolinylamino) |
| Example 111 (89) | MPT0L089 | 21-1242 | (2-isoindolinyl) |
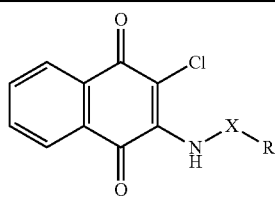
| Example (Compound #) | Code | Number | X | Structure of R |
|---|---|---|---|---|
| Example 112 (90) | MPT0L025 | 31-148 | CO | (4-methoxyphenyl) |

-continued

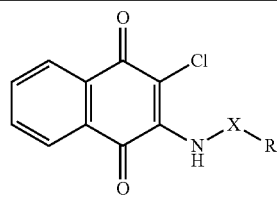

| Example (Compound #) | Code | Number | X | Structure of R |
|---|---|---|---|---|
| Example 113 (91) | MPT0L078 | 31-376 | CH2 | |
| Example 114 (92) | MPT0L077 | 31-398 | CH2 | |

The invention disclosed herein also encompasses prodrugs of the disclosed compounds. Prodrugs are considered to be any covalently bonded carriers that release an active compound of Formula (I) or Formula (II) in vivo. Non-limiting examples of prodrugs include esters of compounds of Formula (I) or Formula (II), and these may be prepared by reacting such compounds with anhydrides such as succinic anhydride.

The invention disclosed herein also encompasses pharmaceutically acceptable salts of the disclosed compounds. In one embodiment, the present invention includes any and all non-toxic, pharmaceutically acceptable salts of the disclosed compounds, comprising inorganic and organic acid addition salts and basic salts. The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (See Pharmaceutical salts, Birge, S. M. et al., J. Pharm. Sci., (1977), 66, 1-19.)

The invention disclosed herein also encompasses solvates of the disclosed compounds. One type of solvate is a hydrate. Solvates typically do not contribute significantly to the physiological activity or toxicity of the compounds and as such can function as pharmacological equivalents.

The invention disclosed herein also encompasses tautomers and isomers of the disclosed compounds. A given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Preparation of the Compounds of the Invention

The compounds of the present invention can be prepared using methods known to those skilled in the art in view of this disclosure. For example, the preferred compounds of the invention can be prepared as shown in the following schemes:

Scheme 1

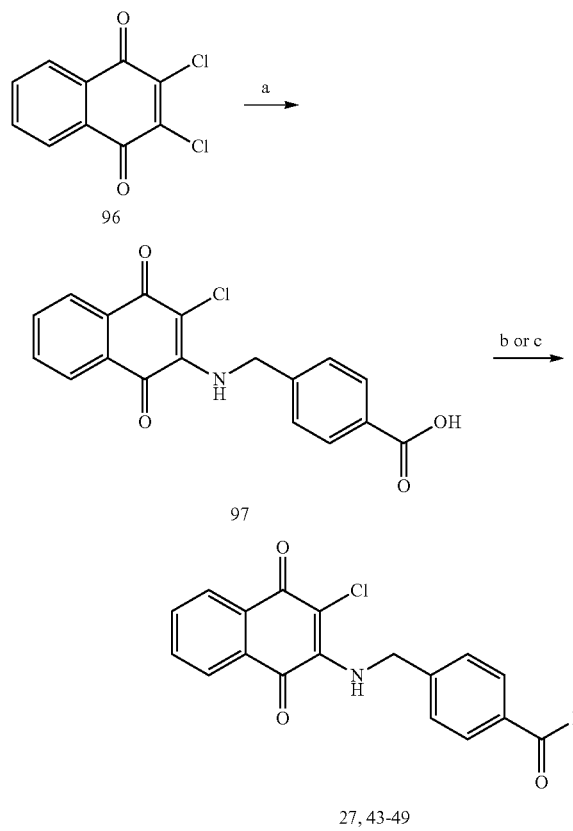

*Reagents and conditions
(a) 4-aminomethylbenzoic acid, TEA, EtOH, reflux.
(b) substituted amine, HBTU, DIPEA, DMF, r.t. for 27, 43, 44
(c) substituted amine, EDC, HCl, HOBt, NMM, DMF, r.t. for 45-49.

Scheme 2

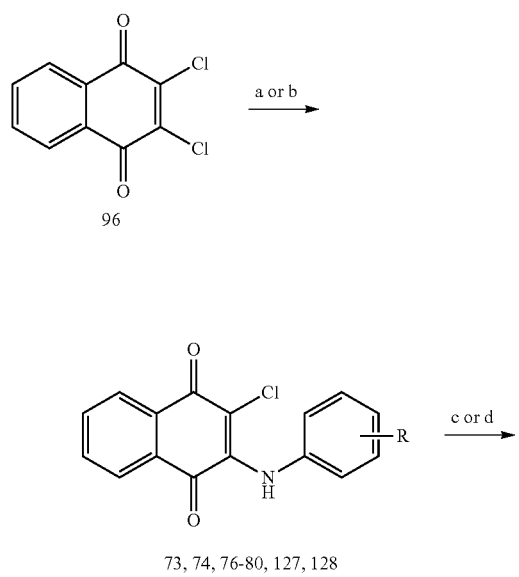

*Reagents and condition
(a) substituted aniline, EtOH, reflux for 76-74, 76-79, 127-128
(b) substituted aniline, $K_2CO_3$, DMF, reflux for 79-80
(c) 4-methoxybenzenesulfonyl chloride, TEA, DCM, r.t. for 71-72
(d) NaH, iodoethane, DMF, r.t. for 75

Scheme 3

*Reagents and condition
(a) substituted amine, ethanol, reflux

Scheme 4

*Reagents and condition
(a) NaH, 4-anisoyl chloride, DMF, rt for 90
(b) substituted benzylamine, EtOH, reflux for 91-92

Pharmaceutical Compositions and Treatments of the Methods of the Invention

Accordingly, the compounds of the invention are potential targets in treatment and/or prevention of neoplastic diseases, neurodegenerative diseases, inflammatory diseases and/or metabolic disorders. In some embodiments, the neoplastic disease includes but is not limited to benign tumor and cancer. In some embodiments, neurodegenerative disease includes but is not limited to ALS, Parkinson's disease, Alzheimer's disease, and Huntington's disease. In some embodiments, autoimmune and inflammatory disease includes but is not limited to insulin-dependent diabetes mellitus (IDDM), diabetes mellitus, multiple sclerosis, experimental autoimmune encephalomyelitis, acute disseminated encephalomyelitis, arthritis, rheumatoid arthritis, experimental autoimmune arthritis, myasthenia gravis, thyroiditis, Hashimoto's disease, primary myxedema, thyrotoxicosis, pernicious anemia, autoimmune atrophic gastritis, Addison's disease, premature menopause, male infertility, juvenile diabetes, goodpasture's syndrome, pemphigus vulgaris, pemphigoid, sympathetic ophthalmia, phacogenic uveitis, autoimmune haemolyticanaemia, idiopathic leucophenia, primary biliary cirrhosis, active chronic hepatitis Hb.sub.s-ve, cryptogenic cirrhosis, ulcerative colitis, Sjogren's syndrome, scleroderma, Wegener's granulomatosis, poly/dermatomyositis, discoid LE, systemic lupus erythematosus, chron's disease, psoriasis, ankylosingspondylitisis, antiphospholipid antibody syndrome, aplastic anemia, autoimmune hepatitis, coeliac disease, graves' disease, guillain-barre syndrome (GBS), Idiopathic thrombocytopenic purpura, opsoclonus myoclonus syndrome (OMS), optic neuritis, ORd's thyroiditis, pemphigus, polyarthritis, primary biliary cirrhosis, Reiter's syndrome, Takayasu's, temporal arteritis, warm autoimmune hemolytic anemia, wegener's granulomatosis, alopecia universalis, behcet's disease, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, inflammatory skin diseases, allergic contact dermatitis, H. pylory gastritis, chronic nasal inflammatory disease, arteriosclerosis and graft versus host disease. In some embodiments, metabolic disorder includes but is not limited to diabetes, high blood pressure, cholesterol, elevated triglyceride level, impaired fasting glucose and insulin resistance.

The compound of the invention is present in the composition in an amount which is effective to treat a particular disorder, including cancers, Parkinson's disease, Alzheimer's disease, and Huntington's disease, restenosis, inflammation, rheumatoid arthritis, inflammatory disorder, tissue injury due to inflammation, hyperproliferative diseases, severe or arthritic psoriasis, muscle-wasting diseases, chronic infectious diseases, abnormal immune response, conditions involving vulnerable plaques, injuries related to ischemic conditions, and viral infection and proliferation.

The compound of the present invention may be administered to a mammal in the form of a raw chemical without any other components present. The compound is preferably administered as part of a pharmaceutical composition containing the compound combined with a suitable pharmaceutically acceptable carrier. Such a carrier can be selected from pharmaceutically acceptable excipients, diluents and auxiliaries.

Pharmaceutical compositions within the scope of the present invention include all compositions where a compound of the present invention is combined with a pharmaceutically acceptable carrier. In a preferred embodiment, the compound is present in the composition in an amount that is effective to achieve its intended therapeutic purpose. While individual needs may vary, a determination of optimal ranges of effective amounts of each compound is within the skill of the art. Typically, the compounds may be administered to a mammal, e.g. a human, at a dose of from about 0.1 to about 100 mg per kg body weight of the mammal, or an equivalent amount of a pharmaceutically acceptable salt, prodrug or solvate thereof, per day to treat, prevent or ameliorate the particular disorder. Preferably, the dose ranges from about 0.1 to about 90 mg, about 0.1 to about 80 mg, about 0.1 to about 70 mg, about 0.1 to about 60 mg, about 0.1 to about 50 mg, about 0.1 to about 40 mg, about 0.1 to about 30 mg, about 0.1 to about 20 mg, about 0.1 to about 10 mg, about 0.1 to about 5 mg, about 0.5 to about 100 mg, about 0.5 to about 90 mg, about 0.5 to about 80 mg, about 0.5 to about 70 mg, about 0.5 to about 60 mg, about 0.5 to about 50 mg, about 0.5 to about 40 mg, about 0.5 to about 30 mg, about 0.5 to about 20 mg, about 0.5 to about 10 mg, about 0.5 to about 5 mg, about 1 to about 100 mg, about 1 to about 90 mg, about 1 to about 80 mg, about 1 to about 70 mg, about 1 to about 60 mg, about 1 to about 50 mg, about 1 to about 40 mg, about 1 to about 30 mg, about 1 to about 20 mg, about 1 to about 10 mg, about 5 to about 100 mg, about 5 to about 90 mg, about 5 to about 80 mg, about 5 to about 70 mg, about 5 to about 60 mg, about 5 to about 50 mg, about 5 to about 40 mg, about 5 to about 30 mg, about 5 to about 20 mg, about 5 to about 10 mg, about 10 to about 100, about 20 to about 100, about 30 to about 100, about 40 to about 100, about 50 to about 100, about 60 to about 100, about 70 to about 100, about 80 to about 100, about 5 to about 90, about 10 to about 90, about 10 to about 80, about 10 to about 70, about 10 to about 60, about 10 to about 50, about 10 to about 40, about 10 to about 30, about 20 to about 90, about 20 to about 80, about 20 to about 70, about 20 to about 60, about 20 to about 50, about 20 to about 40, about 30 to about 90, about 30 to about 80, about 30 to about 70, about 30 to about 60, about 30 to about 50, about 40 to about 90, about 40 to about 80, about 40 to about 60, about 50 to about 90, about 50 to about 80, about 50 to about 70 per kg body weight of the mammal, or an equivalent amount of a pharmaceutically acceptable salt, prodrug or solvate thereof, per day. A useful oral dose of a compound of the present invention administered to a mammal is from about 1 to about 100 mg per kg body weight of the mammal (the preferred dose is as mentioned above), or an equivalent amount of the pharmaceutically acceptable salt, prodrug or solvate thereof. For intramuscular injection, the dose is typically about one-half of the oral dose.

A unit oral dose may comprise from about 5 to about 100 mg, and preferably about 5 to about 100 mg of a compound. The unit dose can be administered one or more times daily, e.g. as one or more tablets or capsules, each containing from about 0.01 mg to about 50 mg of the compound, or an equivalent amount of a pharmaceutically acceptable salt, prodrug or solvate thereof.

The compounds of the present invention may be useful in combination with one or more second therapeutic agents, particularly therapeutic agents suitable for the treatment and/or prevention of the conditions and diseases presented previously.

For example in the cancer treatment, the second therapeutic agent can be a mitotic inhibitor (such as a taxane (preferably paclitaxel or docetaxel), vinca alkaloid (preferably, vinblastine, vincristine, vindesine orvinorelbine) and vepesid; an anthracycline antibiotic (such as doxorubicin, daunorubicin, daunorubicin, epirubicin, idarubicin, valrubicin ormitoxantrone); a nucleoside analog (such as gemcitabine); an EGFR inhibitor (such as gefitinib and erlotinib); an folate antimetabolite (such as trimethoprim, pyrimethamine or pemetrexed); cisplatin or carboplatin. Examples of the second therapeutic agent include but are not limited to tamoxifen, taxol, vinblastine, etoposide (VP-16), adriamycin, 5-fluorouracil (5FU), camptothecin, actinomycin-D, mitomycin C, combretastatin(s), more particularly docetaxel (taxotere), cisplatin (CDDP), cyclophosphamide, doxorubicin, methotrexate, paclitaxel and vincristine, and derivatives and prodrugs thereof.

Further useful second therapeutic agents include compounds that interfere with DNA replication, mitosis, chromosomal segregation and/or tubulin activity. Such compounds include adriamycin, also known as doxorubicin, etoposide, verapamil, podophyllotoxin(s), combretastatin(s) and the like. Agents that disrupt the synthesis and fidelity of polynucleotide precursors may also be used. Particularly useful are agents that have undergone extensive testing and are readily available. As such, agents such as 5-fluorouracil (5-FU) are preferentially used by neoplastic tissue, making this agent particularly useful for targeting neoplastic cells.

The term "angiogenesis" refers to the generation of new blood vessels, generally in a tissue or organ. Under normal physiological conditions, humans or animals undergo angiogenesis only in specific restricted situations. Uncontrolled (persistent and/or unregulated) angiogenesis is related to various disease states, and occurs during tumor development and metastasis. Accordingly, the anti-angiogenesis agent also can be used as the second anti-cancer agent. Other second anti-cancer agents include but are not limited to alkylators such as cyclophosphamide, edelfosine, estramustine and melphalan; antimetabolites such as fluorouracil, methotrexate, mercaptopurine, UFT, tegafur, uracil and cytarabine; anti-tumor Bleomycin, daunorubicin, doxorubicin and epirubicin; antibiotics such as mitomycin and mitoxantrone; topoisomerase such as camptothecin, irinotecan, etoposide, topotecan; taxanes docetaxel, paclitxael, vinca alkaloids, vinblastine, vincristine, cisplatin and octreotide.

Histone deacetylase inhibitors (HDAC inhibitors) also can be used as the second therapeutic agent. Examples include but not limited to hydroxamic acids (or hydroxamates), such as trichostatin A, cyclic tetrapeptides (such as trapoxin B), and depsipeptides, benzamides, electrophilic ketones, and aliphatic acid compounds such as phenylbutyrate and valproic acid.

For example in inflammation treatment, the second therapeutic agent includes, but is not limited to, corticosteroid, a lubricant, a keratolytic agent, a vitamin $D_3$ derivative, PUVA and anthralin, $\beta_2$-agonist and a corticosteroid.

For example in autoimmune disease treatment, the second therapeutic agent includes, but is not limited to, immunosuppressants, NSAIDs, COX-2 inhibitors, biologics, non-steroidal calcineurin inhibitors, steroidal anti-inflammatory agents, 5-amino salicylic acid, DMARDs, hydroxychloroquine sulfate, inflammatory modulators, agents that interfere with B cell action, and penicillamine.

Pharmaceutically acceptable carriers and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a compound of the invention, diluents, dispersing and surface active agents, binders, and lubricants. One skilled in this art may further formulate the compound of the invention in an appropriate manner, and in accordance with accepted practices, such as those disclosed in Remington's Pharmaceutical Sciences, Gennaro, Ed., Mack Publishing Co., Easton, Pa. 1990.

In one aspect, the present invention provides a method for treating a disease in association with block of ubiquitination-proteasome system in a subject, comprising administering to the subject an effective amount of the compound of the invention. The disease includes but is not limited to cancer and related conditions as discussed above. Accordingly, first, the invention provides a method for treating a cancer in a subject, comprising administering to the subject an effective amount of the compound of the invention. Such method includes administering a compound of the present invention to a subject in an amount sufficient to treat the condition. For example, the cancers include but are not limited to the group consisting of: neuroblastoma; lung cancer; bile duct cancer; non small cell lung carcinoma; hepatocellular carcinoma; head and neck squamous cell carcinoma; squamous cell cervical carcinoma; lymphoma; nasopharyngeal carcinoma; gastric cancer; colon cancer; uterine cervical carcinoma; gall bladder cancer; prostate cancer; breast cancer; testicular germ cell tumors; colorectal cancer; glioma; thyroid cancer; basal cell carcinoma; gastrointestinal stromal cancer; hepatoblastoma; endometrial cancer; ovarian cancer; pancreatic cancer; renal cell cancer, Kaposi's sarcoma, chronic leukemia, sarcoma, rectal cancer, throat cancer, melanoma, colon cancer, bladder cancer, mastocytoma, mammary carcinoma, mammary adenocarcinoma, pharyngeal squamous cell carcinoma, testicular cancer, gastrointestinal cancer, or stomach cancer and urothelial cancer.

In a further aspect, the present invention provides a method for treating inflammatory disorders and autoimmune disorders and related conditions as discussed above. Such methods include administering a compound of the present invention to a subject in an amount sufficient to treat the condition. Preferably, the disorders are restenosis, inflammation, rheumatoid arthritis, tissue injury due to inflammation, hyperproliferative diseases, severe or arthritic psoriasis, muscle-wasting diseases, chronic infectious diseases, abnormal immune response, conditions involving vulnerable plaques, injuries related to ischemic conditions, and viral infection or proliferation.

The dose range of the compounds of general formula (I) applicable per day is usually from 5 to 100 mg, preferably from 5 to 100 mg per kg body weight of the patient. Each dosage unit may conveniently contain from 5 to 100 mg of a compound according to the invention.

The actual therapeutically effective amount or therapeutic dosage will of course depend on factors known by those skilled in the art such as age and weight of the patient, route of administration and severity of disease. In any case, the combination will be administered at dosages and in a manner which allow a therapeutically effective amount to be delivered based upon subject's unique condition.

For oral administration, suitable pharmaceutical compositions of the invention include powders, granules, pills, tablets, lozenges, chews, gels, and capsules as well as liquids, syrups, suspensions, elixirs, and emulsions. These compositions may also include anti-oxidants, flavorants, preservatives, suspending, thickening and emulsifying agents, colorants, flavoring agents and other pharmaceutically acceptable additives. Formulations for oral administration may be formulated to be immediate release or modified release, where modified release includes delayed, sustained, pulsed, controlled, targeted and programmed release.

For parenteral administration, the compounds of the present invention are administered directly into the blood stream, into muscle, or into an internal organ via an intravenous, intraarterial, intraperitoneal, intramuscular, subcutaneous or other injection or infusion. Parenteral formulations may be prepared in aqueous injection solutions which may contain, in addition to the compound of the invention, buffers, antioxidants, bacteriostats, salts, carbohydrates, and other additives commonly employed in such solutions. Parenteral administrations may be immediate release or modified release (such as an injected or implanted depot).

Compounds of the present invention may also be administered topically, (intra)dermally, or transdermally to the skin or mucosa. Typical formulations include gels, hydrogels, lotions, solutions, creams, ointments, dressings, foams, skin patches, wafers, implants and microemulsions. Compounds of the present invention may also be administered via inhalation or intranasal administration, such as with a dry powder, an aerosol spray or as drops. Additional routes of administration for compounds of the present invention include intravaginal and rectal (by means of a suppository, pessary or enema), and ocular and aural.

Biological Assay

Blocking of ITCH Self-Ubiquitination

The compounds of the invention and a control compound (such as Compound 44 of WO 2010/005534) as a comparative compound were used to test the blocking of ITCH self-ubiquitination. The results show that the compounds of the invention blocks ITCH self-ubiquitnation (Lys-dependent) more efficiently than the control compound (see FIG. 1). [Reference for in vitro assay: Scialpi F, Malatesta M, Peschiaroli A, Rossi M, Melino G, and Bernassola F. Itch self-polyubiquitylation occurs through lysine-63 linkages. Biochem Pharmacol. 2008 Dec. 1; 76(11):1515-21. Reference for in vivo assay: Chang L, Kamata H, Solinas G, Luo JL, Maeda S, Venuprasad K, Liu YC, and Karin M. The E3 ubiquitin ligase itch couples JNK activation to TNFalpha-induced cell death by inducing c-FLIP(L) turnover. Cell. 2006 Feb. 10; 124(3):601-13.]

Antiproliferative Activity Against Human Normal and Cancer Cell Lines Using Growth Inhibition Assay ($GI_{50}$)

The compounds of the invention were subjected to growth inhibition assay. Cells were seeded in 96-well plastic plates and exposed to MPT0L132, MPT0L133, and MPT0L134 for 48 hours. Cell viability was assessed using the 3-(4,5-dimethylthiazol-2-yl)-2,5-diphenyltetrazolium bromide assay. Growth inhibition was expressed as the percentage of surviving cells in drug-treated versus DMSO-treated control cells. The results are shown as follows.

| Compounds | HL-60 $IC_{50}$ (μM) Mean ± S.E. | HCT-116 | MDA-MB-231 $GI_{50}$ (μM) Mean ± S.E. | Hep3B |
|---|---|---|---|---|
| MPT0L132 | 2.50 ± 0.15 | 3.69 ± 0.24 | 10~30 | 10~30 |
| MPT0L133 | 1.67 ± 0.27 | 4.04 ± 0.65 | 10~30 | 10~30 |
| MPT0L134 | 2.52 ± 0.12 | 3.53 ± 0.24 | 10~30 | 10~30 |

Effects of the Compounds of the Invention on IL-6 Production in murineRAW264.7 Macrophage Cells Cell Culture. The RAW264.7 mouse macrophage cells were purchased from the Bioresource Collection and Research Center (Hsinchu, Taiwan) and the cells cultured at 37° C. in 5% CO2/95% air in, respectively, 90% Ham's F-12 or Dulbecco's modified Eagle medium, both containing 10% heat-inactivated fetal bovine serum (FBS) (Invitrogen Life Technologies, Carlsbad, Calif.) and 1% penicillin/streptomycin (Biological Industries, Israel).

IL-6 Determination. To determine the effect of MPT0L 132, MPT0L133 and MPT0L134 on the production of cytokine IL-6 from LPS-stimulated cells, RAW 264.7 cells ($1 \times 10^6$) were plated and pretreated in the presence or absence of MPT0L 132, MPT0L133 and MPT0L134 for 1 h, and then stimulated with LPS (25 ng/mL) for 24 h at 37° C. Supernatants were collected and the concentrations of cytokines IL-6 was measured by ELISA kit.

Effects of the Compounds of the Invention on IL-6 Production in Human RAFLS (Rheumatoid Arthritis Fibroblast-Like synoviocytes) Cells Cell Culture. Human rheumatoid arthritis fibroblast-like synoviocytes (RAFLS) from Cell Application Inc. (San Diego, Calif., USA) were grown in synoviocytes growth medium from the same supplier.

IL-6 Determination. RA-FLS ($2.5 \times 10^4$) was treated with various concentrations of MPT0L132, MPT0L133 and MPT0L134 for 24 h, then the medium was collected and assayed for IL-6 using commercial ELISA kit.

The Compounds of the Invention Inhibit Development of Arthritis in an Adjuvant-Induced Arthritis (AIA) Model In Vivo Adjuvant-Induced Arthritis (AIA) Model. Five-week-old male Lewis rats were obtained from the National Laboratory Animal Center (Taipei, Taiwan). Complete Freund's adjuvant (CFA) was prepared by suspending heat-killed *Mycobacterium butyricum* (Difco) in mineral oil at 3 mg/mL. CFA-induced arthritis was induced by intradermal injection of 100 μL of the CFA emulsion into the base of the right hind paw on day 0. MPT0L132, MPT0L133 and MPT0L134 (each for 25 mg/kg, po, qd), Bortezomib (1 mg/kg, ip, qwk), positive control indomethacin (1 mg/kg, po, qwk), or vehicle was given by gavage from day 2 to day 21. On days 0, 2, 6, 9, 13, 17, and 21, the animals were weighed and both hind paw volumes measured using a digital plethysmometer (Diagnostic & Research Instruments Co. Ltd, Taipei, Taiwan). On day 21, micro-computed tomography (micro-CT) of the paws was performed by the Core Facilities Center of the National Research Program for Biopharmaceuticals using an in vivo micro-CT scanner (Skyscan 1176, Bruker Corp., Kontich, Belgium) at 18 μm resolution and 180° scanning with a rotation step of 0.8o per image, 300 msec integration time, 70 keV photon energy, and 350 μA current.

Treatment with the Compounds of the Invention to Prevent Bone Mineral Density (BMD) and Bone Mineral Content (BMC) Loss in AIA Model Quantification of volumetric bone mineral density (BMD) and bone volume (BV) was performed in a defined bone area ranging 12 mm from tarsals to the end of the calcaneus. The bone mineral content (BMC) was described by the product of BV and BMD.

EXAMPLES

Example 25 4-(((3-chloro-1,4-dioxo-1,4-dihydronaphthalen-2-yl)amino)methyl)-N-(pyridin-4-ylmethyl)benzamide (27)

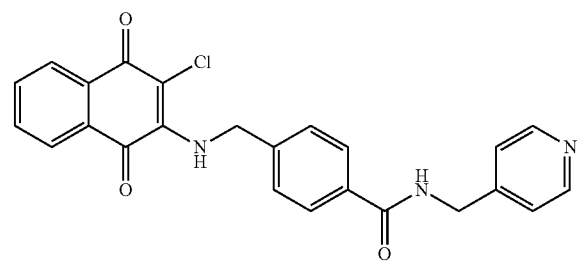 [SMILES: O=C(NCc1ccncc1)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 4-aminomethylpyridine (0.13 ml, 1.32 mmol) at room temperature and stirred overnight. The residue was purified by flash column over silica gel (dichloromethane:methanol=9:1, Rf=0.48) to afford 27 (0.31 g, 81.57%) as a red solid. $^1$H-NMR (300 MHz, DMSO-$d_6$): δ 4.47 (d, J=6.0 Hz, 2H), 5.01 (s, 1H), 7.28 (d, J=5.7 Hz, 2H), 7.41 (d, J=8.1 Hz, 2H), 7.75 (t, J=6.3 Hz, 1H), 7.80-7.87 (m, 3H), 7.97 (d, J=7.8 Hz, 2H), 8.08 (s, 1H), 8.48 (d, J=6.0 Hz, 2H), 9.08 (t, J=6.0 Hz, 1H).

Example 41 4-(((3-chloro-1,4-dioxo-1,4-dihydronaphthalen-2-yl)amino)methyl)-N-(2-morpholinoethyl)benzamide (43)

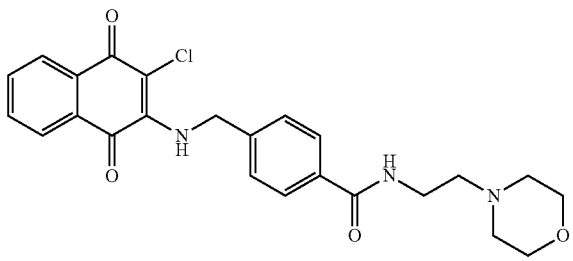 [SMILES: O=C(NCCN1CCOCC1)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.13 ml, 1.32 mmol) and DMF (2.5 ml) was stirred for a while, to which was then added 2-morpholinoethanamine (0.17 ml, 1.32 mmol) at room temperature, and the mixture was stirred overnight. The residue was filtered by suction filtration to yield a red product. The residue was without further purification to afford 43 (0.23 g, 57.58%) as a red solid. $^1$H-NMR (300 MHz, DMSO-$d_6$): δ 2.38-2.45 (m, 6H), 3.54 (s, 4H), 4.99 (s, 2H), 7.36 (d, J=8.1 Hz, 2H), 7.71-7.84 (m, 4H), 7.96 (d, J=7.5 Hz, 2H), 8.05 (s, 1H), 8.33 (t, J=5.1 Hz, 1H).

Example 42 N-(2-(1H-indol-3-yl)ethyl)-4-(((3-chloro-1,4-dioxo-1,4-dihydronaphthalen-2-yl)amino)methyl)benzamide (44)

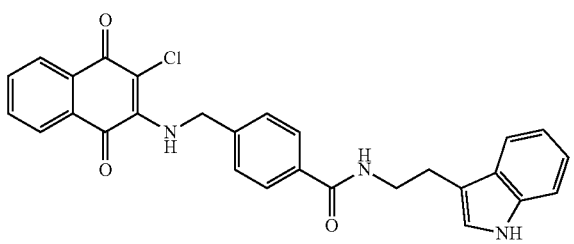 [SMILES: O=C(NCCc1c[nH]c2ccccc12)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.13 ml, 1.32 mmol) and DMF (2.5 ml) was stirred for a while, to which was then added tryptamine (0.21 g, 1.32 mmol) at room temperature and stirred overnight. The residue was purified by flash column over silica gel (ethyl acetate:n-hexane=2:1, Rf=0.45) to afford 44 (0.13 g, 30.53%) as a red solid. $^1$H-NMR (300 MHz, DMSO-$d_6$): δ 2.72-2.94 (m, 2H), 3.47-3.54 (m, 2H), 4.99 (s, 2H), 6.92-6.98 (m, 1H), 7.01-7.07 (m, 1H), 7.15 (d, J=2.4 Hz, 1H), 7.31 (d, J=8.1 Hz, 1H), 7.36 (d, J=8.1 Hz, 2H), 7.55 (d, J=7.5 Hz, 1H), 7.73-7.82 (m, 4H), 7.96 (d, J=8.1 Hz, 2H), 8.06 (s, 1H), 8.54 (t, J=5.7 Hz, 1H), 10.78 (s, 1H).

Example 43 4-(((3-chloro-1,4-dioxo-1,4-dihydronaphthalen-2-yl)amino)methyl)-N-(2-(dimethylamino)ethyl)benzamide (45)

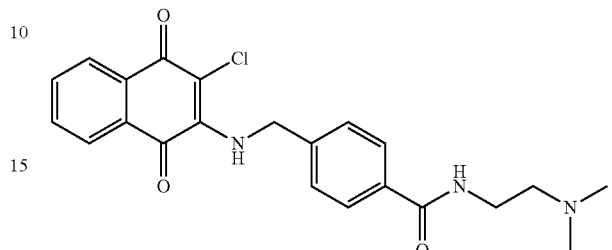

A mixture of 97 (0.30 g, 0.88 mmol), EDC.HCl (0.25 g, 1.32 mmol), HOBt (0.14 g, 1.06 mmol), NMM (0.23 ml, 2.11 mmol) and DMF (2.5 ml) was stirred for a while, to which was then added 2-dimethylaminoethylamine (0.12 ml, 1.06 mmol) at room temperature and stirred overnight. The residue was purified by flash column over silica gel (dichloromethane:methanol=9:1, Rf=0.33) to afford 45 (0.05 g, 13.79%) as a red solid. $^1$H-NMR (300 MHz, CD$_3$OD): δ 2.92 (s, 6H), 3.72 (t, J=6.0 Hz, 2H), 5.10 (s, 2H), 7.44 (d, J=8.4 Hz, 2H), 7.68-7.81 (m, 2H), 7.85 (d, J=8.4 Hz, 2H), 8.02-8.06 (m, 2H).

Example 44 4-(((3-chloro-1,4-dioxo-1,4-dihydronaphthalen-2-yl)amino)methyl)-N-(2-(pyrrolidin-1-yl)ethyl)benzamide (46)

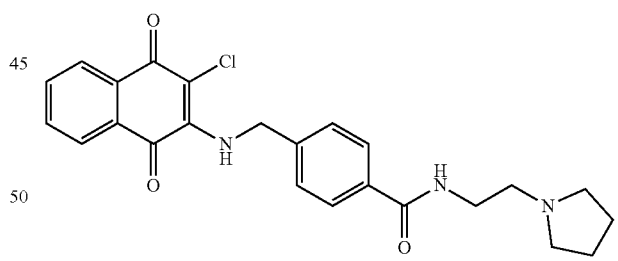

A mixture of 97 (0.30 g, 0.88 mmol), EDC.HCl (0.25 g, 1.32 mmol), HOBt (0.14 g, 1.06 mmol), NMM (0.23 ml, 2.11 mmol) and DMF (2.5 ml) was stirred for a while, to which was then added 2-(pyrrolidin-1-yl)ethanamine (0.13 ml, 1.06 mmol) at room temperature and stirred overnight. The residue was purified by flash column over silica gel (dichloromethane:methanol=9:1, Rf=0.33) to afford 46 (0.22 g, 57.09%) as a red solid. $^1$H-NMR (300 MHz, DMSO-$d_6$): δ 1.89 (s, 4H), 3.22-3.25 (m, 5H), 3.54-3.60 (m, 3H), 5.00 (t, J=7.2 Hz, 2H), 7.38 (d, J=8.1 Hz, 2H), 7.72-7.82 (m, 2H), 7.85 (d, J=8.4 Hz, 2H), 7.94-7.98 (m, 2H), 8.08 (t, J=7.2 Hz, 1H), 8.74 (t, J=5.7 Hz, 1H).

Example 45 4-(((3-chloro-1,4-dioxo-1,4-dihydronaphthalen-2-yl)amino)methyl)-N-(2-(diethylamino)ethyl)benzamide (47)

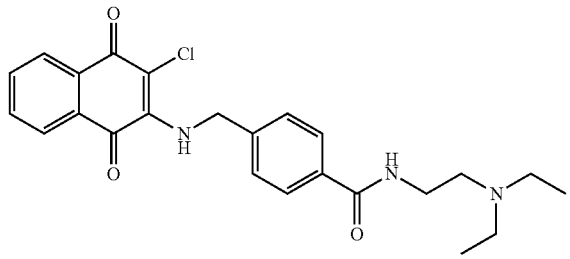 [SMILES: CCN(CC)CCNC(=O)c1ccc(CNC2=C(Cl)C(=O)c3ccccc3C2=O)cc1]

A mixture of 97 (0.30 g, 0.88 mmol), EDC.HCl (0.25 g, 1.32 mmol), HOBt (0.14 g, 1.06 mmol), NMM (0.23 ml, 2.11 mmol) and DMF (2.5 ml) was stirred for a while, to which was then added 2-diethylaminoethylamine (0.15 ml, 1.06 mmol) at room temperature and stirred overnight. The residue was purified by flash column over silica gel (dichloromethane:methanol=9:1, Rf=0.30) to afford 47 (0.06 g, 15.50%) as a red solid. $^1$H-NMR (300 MHz, CD$_3$OD): δ 1.33 (t, J=7.2 Hz, 6H), 3.32-3.38 (m, 3H), 3.73 (t, J=6.0 Hz, 2H), 5.10 (s, 2H), 7.45 (d, J=8.1 Hz, 2H), 7.67-7.80 (m, 2H), 7.85 (d, J=8.1 Hz, 2H), 8.02-8.06 (m, 2H).

Example 46 4-(((3-chloro-1,4-dioxo-1,4-dihydronaphthalen-2-yl)amino)methyl)-N-(2-(piperidin-1-yl)ethyl)benzamide (48)

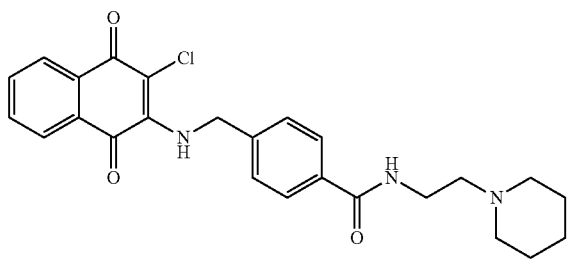 [SMILES: O=C(NCCN1CCCCC1)c1ccc(CNC2=C(Cl)C(=O)c3ccccc3C2=O)cc1]

A mixture of 97 (0.30 g, 0.88 mmol), EDC.HCl (0.25 g, 1.32 mmol), HOBt (0.14 g, 1.06 mmol), NMM (0.23 ml, 2.11 mmol) and DMF (2.5 ml) was stirred for a while, to which was then added 2-(piperidin-1-yl)ethanamine (0.15 ml, 1.06 mmol) at room temperature and stirred overnight. The residue was purified by flash column over silica gel (dichloromethane:methanol=9:1, Rf=0.55) to afford 48 (0.08 g, 20.11%) as a red solid. $^1$H-NMR (300 MHz, DMSO-d$_6$): δ 1.42-1.44 (m, 2H), 1.58-1.60 (m, 4H), 2.78 (br, 6H), 3.44-3.48 (m, 2H), 4.99 (d, J=7.2 Hz, 2H), 7.37 (d, J=8.4 Hz, 2H), 7.71-7.84 (m, 4H), 7.94-7.97 (m, 2H), 8.07 (t, J=7.2 Hz, 1H), 8.53 (br, 1H).

Example 47 4-(((3-chloro-1,4-dioxo-1,4-dihydronaphthalen-2-yl)amino)methyl)-N-(2-(4-methylpiperazin-1-yl)ethyl)benzamide (49)

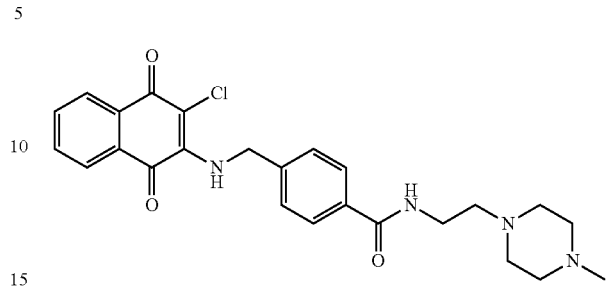

A mixture of 97 (0.30 g, 0.88 mmol), EDC.HCl (0.25 g, 1.32 mmol), HOBt (0.14 g, 1.06 mmol), NMM (0.23 ml, 2.11 mmol) and DMF (2.5 ml) was stirred for a while, to which was then added 2-(4-methylpiperazin-1-yl)ethylamine (0.16 ml, 1.06 mmol) at room temperature and stirred overnight. The residue was purified by flash column over silica gel (dichloromethane:methanol=9:1, Rf=0.19) to afford 49 (0.08 g, 19.47%) as a red solid. $^1$H-NMR (300 MHz, DMSO-d$_6$): δ 2.13 (s, 3H), 2.36-2.42 (br, 12H), 4.91 (d, J=6.3 Hz, 2H), 7.29 (d, J=7.8 Hz, 2H), 7.67-7.77 (m, 4H), 7.88 (d, J=6.9 Hz, 2H), 7.98 (br, 1H), 8.25 (br, 1H).

Example 92 N-(4-((3-chloro-1,4-dioxo-1,4-dihydronaphthalen-2-yl)amino)phenyl)-4-methoxybenzenesulfonamide (71)

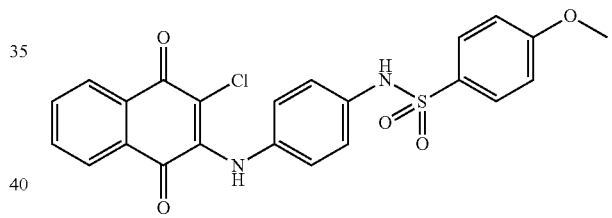

Compound 127 (0.1 g, 0.33 mmol) was dissolved in dichloromethane (10 ml) and to which was then added triethylamine (0.01 ml, 0.07 mmol) and 4-methoxybenzenesulfonyl chloride (0.07 g, 0.34 mmol). The reaction mixture was stirred at room temperature for 2 days. The residue was purified by flash column over silica gel (ethyl acetate:n-Hexane=1:2, Rf=0.14) to afford 71 (0.01 g, 6.68%) as a red solid. $^1$H-NMR (500 MHz, d-Acetone): δ 3.85 (s, 3H), 7.01 (d, J=9.0 Hz, 2H), 7.09 (d, J=9.0 Hz, 2H), 7.16 (d, J=9.0 Hz, 2H), 7.69 (d, J=8.5 Hz, 2H), 7.79-7.86 (m, 2H), 8.08 (d, J=9.0 Hz, 2H).

Example 93 2-((3-aminophenyl)amino)-3-chloronaphthalene-1,4-dione (73)

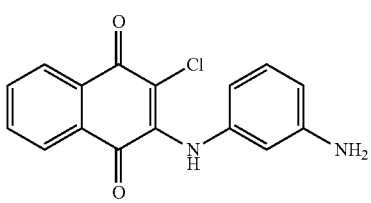 [SMILES: Nc1cccc(NC2=C(Cl)C(=O)c3ccccc3C2=O)c1]

A mixture of 2,3-dichloro-1,4-naphthoquinone (2.14 g, 9.43 mmol) and benzene-1,3-diamine (1.50 g, 9.25 mmol) and ethanol (25 mL) was refluxed overnight. The solution was evaporated to give a residue, which was purified by flash column over silica gel (EtOAc:n-hexane=1:2, Rf=0.33) to afford 73 (0.90 g, 32.57%). $^1$H NMR (300 MHz, DMSO-$d_6$): δ 6.39 (s, 1H), 7.09-7.16 (m, 1H), 7.61 (brs, 1H), 7.66-7.83 (m, 3H), 8.10-8.15 (m, 1H), 8.17-8.22 (m, 2H).

Example 94 N-(3-((3-chloro-1,4-dioxo-1,4-dihydronaphthalen-2-yl)amino)phenyl)-4-methoxybenzenesulfonamide (72)

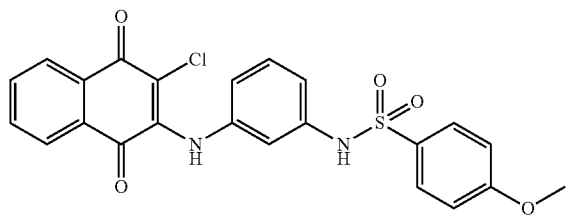 [SMILES: COc1ccc(S(=O)(=O)Nc2cccc(NC3=C(Cl)C(=O)c4ccccc4C3=O)c2)cc1]

Compound 73 (0.1 g, 0.33 mmol) was dissolved in dichloromethane (5 ml) and to which was then added triethylamine (0.01 ml, 0.07 mmol) and 4-methoxybenzenesulfonyl chloride (0.07 g, 0.34 mmol). The reaction mixture was stirred at room temperature for 2 days. The residue was purified by flash column over silica gel (ethyl acetate:n-Hexane=1:2, Rf=0.19) to afford 72 (0.01 g, 6.68%) as a red solid. $^1$H-NMR (300 MHz, CDCl$_3$): δ 3.85 (s, 3H), 6.51 (brs, 1H), 6.82-6.92 (m, 5H), 7.21 (t, J=8.4 Hz, 1H), 7.56 (s, 1H), 7.68-7.73 (m, 3H), 7.78 (t, J=7.5 Hz, 1H), 8.12 (d, J=7.5 Hz, 1H), 8.18 (d, J=7.5 Hz, 1H).

Example 96 2-chloro-3-((4-fluorophenyl)amino)naphthalene-1,4-dione (128)

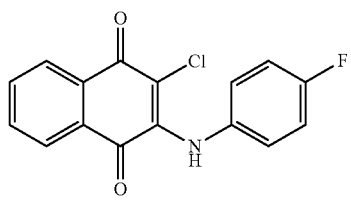 [SMILES: O=C1C(Cl)=C(Nc2ccc(F)cc2)C(=O)c2ccccc21]

A mixture of 2,3-dichloro-1,4-naphthoquinone (0.50 g, 2.20 mmol) and 4-fluoroaniline (0.43 ml, 4.40 mmol) and ethanol (5 ml) was refluxed for 16 h. The reaction mixture was filtered and washed by dichloromethane, ethyl acetate and methanol. The residue was without further purification to afford 128 (0.20 g, 30.30%). $^1$H NMR (300 MHz, DMSO-$d_6$): δ 7.15-7.17 (m, 4H), 7.77-7.89 (m, 2H), 8.03 (d, J=7.8 Hz, 2H), 9.29 (s, 1H).

Example 97 2-Chloro-3-(ethyl(4-fluorophenyl)amino)naphthalene-1,4-dione (75)

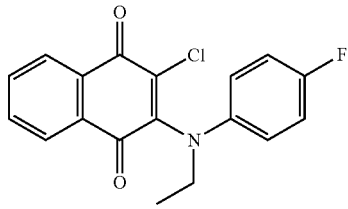 [SMILES: CCN(C1=C(Cl)C(=O)c2ccccc2C1=O)c1ccc(F)cc1]

Compound 128 (0.20 g, 0.66 mmol) was dissolved in DMF (1 mL) and added NaH (0.04 g, 0.86 mmol) then stirred for while and to which was then added iodoethane (0.08 ml, 0.99 mmol) slowly at 0° C. The reaction mixture was warmed to room temperature, and stirring was continued for another 1 h. The residue was purified by flash column over silica gel (EtOAc:n-hexane=1:9) to afford compound 75 (0.01 g, 4.59%). $^1$H NMR (300 MHz, CDCl$_3$): δ 1.32 (t, J=6.9 Hz, 3H), 3.92 (q, J=7.2 Hz, 2H), 6.86-6.89 (m, 2H), 6.98-7.01 (m, 2H), 7.68-7.78 (m, 2H), 7.99-8.02 (m, 1H), 8.16-8.19 (m, 1H).

Example 98 2-Chloro-3-((4-(4-methylpiperazin-1-yl)phenyl)amino)naphthalene-1,4-dione (76)

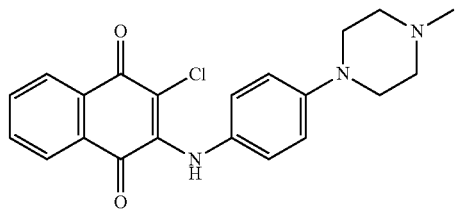 [SMILES: CN1CCN(c2ccc(NC3=C(Cl)C(=O)c4ccccc4C3=O)cc2)CC1]

A mixture of 2,3-dichloro-1,4-naphthoquinone (0.37 g, 1.60 mmol) and 4-(4-methylpiperazin-1-yl)aniline (0.3 g, 1.46 mmol) was dissolved in EtOH (5 ml). The reaction mixture was stirred and refluxed for 16 h. The residue was purified by flash column over silica gel (dichloromethane:methanol=29:1) to afford 76 (0.12 g, 21.52%). $^1$H NMR (300 MHz, CDCl$_3$): δ 2.36 (s, 3H), 2.58 (t, J=6.0 Hz, 4H), 3.23 (t, J=6.0 Hz, 4H), 6.88 (d, J=9.0 Hz, 2H), 7.01 (d, J=8.7 Hz, 2H), 7.65-7.77 (m, 3H), 8.10 (d, J=7.5 Hz, 1H), 8.18 (d, J=7.5 Hz, 1H).

Example 99 2-Chloro-3-((4-(4-ethylpiperazin-1-yl)phenyl)amino)naphthalene-1,4-dione (77)

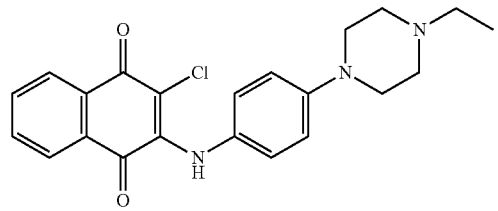 [SMILES: CCN1CCN(c2ccc(NC3=C(Cl)C(=O)c4ccccc4C3=O)cc2)CC1]

A mixture of 2,3-dichloro-1,4-naphthoquinone (0.37 g, 1.60 mmol) and 4-(4-ethylpiperazin-1-yl)aniline (0.3 g, 1.46 mmol) was dissolved in EtOH (5 ml). The reaction was stirred and refluxed for 16 h. The residue was purified by flash column over silica gel (dichloromethane:methanol=29:1) to afford 77 (0.10 g, 17.30%). $^1$H NMR (300 MHz, CDCl$_3$): δ 1.15 (t, J=6.0 Hz, 3H), 2.48 (t, J=6.0 Hz, 2H), 2.63 (t, J=6.0 Hz, 4H), 3.26 (t, J=6.0 Hz, 4H), 6.89 (d, J=9.0 Hz, 2H), 7.03 (d, J=8.7 Hz, 2H), 7.65-7.70 (m, 2H), 7.77-7.79 (m, 1H), 8.10-8.13 (m, 1H), 8.18-8.20 (m, 1H).

Example 100 2-chloro-3-((2-fluoro-4-iodophenyl)amino)naphthalene-1,4-dione (78)

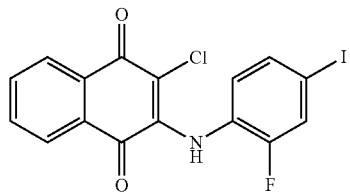 [SMILES: O=C1C(Cl)=C(Nc2ccc(I)cc2F)C(=O)c2ccccc21]

A mixture of 2,3-dichloro-1,4-naphthaquinone (0.20 g, 0.88 mmol) and 2-fluoro-4-iodoaniline (0.19 g, 0.80 mmol) was dissolved in EtOH (15 ml) and stirred and refluxed for 3 day. The residue was purified by flash column over silica gel (ethyl acetate:n-Hexane=1:9, Rf=0.25) to afford 78 (0.08 g, 23.39%) as a red solid. $^1$H-NMR (300 MHz, DMSO-d$_6$): δ 7.09 (t, J=8.4 Hz, 1H), 7.54 (m, 1H), 7.65 (m, 1H), 7.83 (m, 2H), 8.01 (m, 2H), 9.22 (br, 1H).

Example 101 2-chloro-3-((2,4,6-trichloro-3,5-dimethoxyphenyl)amino)naphthalene-1,4-dione (79)

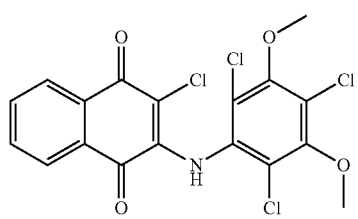 [SMILES: COc1c(Cl)c(NC2=C(Cl)C(=O)c3ccccc3C2=O)c(Cl)c(OC)c1Cl]

A mixture of 2,3-dichloro-1,4-naphthaquinone (0.20 g, 0.88 mmol), potassium carbonate (0.17 g, 1.20 mmol) and 2,4,6-chloro-3,5-methoxyaniline (0.21 g, 0.80 mmol) was dissolved in DMF (2 ml) and stirred at 120° C. overnight. The residue was purified by flash column over silica gel (ethyl acetate:n-Hexane=1:15, Rf=0.15) to afford 79 (0.18 g, 50.32%) as a yellow solid. $^1$H-NMR (300 MHz, CDCl$_3$): δ 3.93 (s, 6H), 7.31 (s, 1H), 7.76 (m, 2H), 8.15 (m, 1H), 8.19 (m, 1H).

Example 102 2-((3-chloro-1,4-dioxo-1,4-dihydronaphthalen-2-yl)amino)-5-iodobenzonitrile (80)

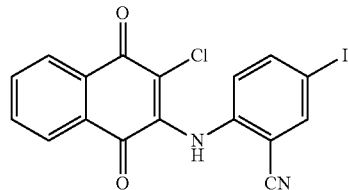 [SMILES: N#Cc1cc(I)ccc1NC1=C(Cl)C(=O)c2ccccc2C1=O]

A mixture of 2,3-dichloro-1,4-naphthaquinone (0.20 g, 0.88 mmol), potassium carbonate (0.17 g, 1.20 mmol) and 2-amino-5-iodobenzonitrile (0.20 g, 0.80 mmol) was dissolved in DMF (2 ml) and stirred at 120° C. overnight. The residue was purified by flash column over silica gel (ethyl acetate:n-Hexane=1:9, Rf=0.05) to afford 80 (0.15 g, 43.14%) as a yellow solid. $^1$H-NMR (300 MHz, CDCl$_3$): δ 6.80 (s, 1H), 7.60 (s, 1H), 7.79 (m, 3H), 7.94 (m, 1H), 8.17 (m, 1H), 8.20 (m, 1H).

Example 103 2-Chloro-3-((quinolin-6-yl)amino)naphthalene-1,4-dione (81)

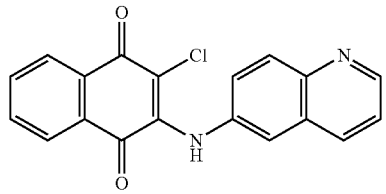 [SMILES: O=C1C(Cl)=C(Nc2ccc3ncccc3c2)C(=O)c2ccccc21]

A mixture of 2,3-dichloro-1,4-naphthoquinone (0.50 g, 2.20 mmol) and 6-aminoquinoline (0.63 g, 4.40 mmol) was dissolved in ethanol (5 ml). The reaction mixture was refluxed for 16 h. The residue was filtered and washed by dichloromethane, ethyl acetate and methanol. The product was without more purification to afford 81 (0.38 g, 51.60%). $^1$H NMR (300 MHz, DMSO-d$_6$): δ 7.50 (q, J=4.2 Hz, 1H), 7.56-7.62 (m, 2H), 7.79-7.93 (m, 3H), 8.03 (q, J=7.5 Hz, 2H), 8.26 (d, J=7.5 Hz, 1H), 8.78-8.80 (m, 1H).

Example 104 2-Chloro-3-(quinolin-3-ylamino)naphthalene-1,4-dione (82)

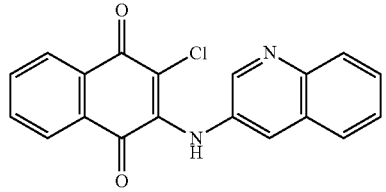 [SMILES: O=C1C(Cl)=C(Nc2cnc3ccccc3c2)C(=O)c2ccccc21]

A mixture of 2,3-dichloro-1,4-naphthoquinone (0.50 g, 2.20 mmol) and 3-aminoquinoline (0.63 g, 4.40 mmol) was dissolved in ethanol (5 ml). The reaction mixture was refluxed for 16 h. The residue was filtered and washed by dichloromethane, ethyl acetate and methanol. The product was without more purification to afford 82 (0.31 g, 42.09%).

$^1$H NMR (300 MHz, DMSO-d$_6$): δ 7.57 (t, J=7.2 Hz, 1H), 7.64-7.69 (m, 1H), 7.77-7.91 (m, 4H), 7.97 (d, J=8.1 Hz, 1H), 8.00-8.04 (m, 2H).

Example 105 2-Chloro-3-(quinolin-5-ylamino)naphthalene-1,4-dione (83)

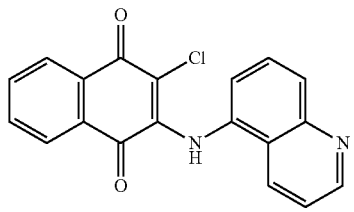 [SMILES: O=C1C(Cl)=C(Nc2cccc3ncccc23)C(=O)c2ccccc21]

A mixture of 2,3-dichloro-1,4-naphthoquinone (0.50 g, 2.20 mmol) and 5-aminoquinoline (0.63 g, 4.40 mmol) was dissolved in ethanol (5 ml). The reaction mixture was refluxed for 16 h. The residue was filtered and washed by dichloromethane, ethyl acetate and methanol. The product was without more purification to afford 83 (0.46 g, 62.46%). $^1$H NMR (300 MHz, CDCl$_3$): δ 7.24-7.27 (m, 1H), 7.48 (q, J=4.2 Hz, 1H), 7.68-7.82 (m, 4H), 8.08 (d, J=9.0 Hz, 1H), 8.15-8.22 (m, 2H), 8.33-8.36 (m, 1H), 8.97-8.98 (m, 1H).

Example 106 2-((1H-indol-6-yl)amino)-3-chloronaphthalene-1,4-dione (84)

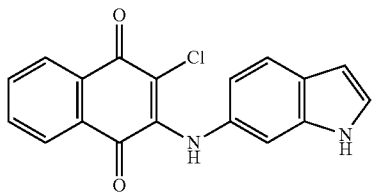 [SMILES: O=C1C(Cl)=C(Nc2ccc3cc[nH]c3c2)C(=O)c2ccccc21]

Compound 6-nitroindole (0.30 g, 1.85 mmol) was dissolved in ethanol (10 ml) and added the 10% Pd/C as catalyst. The reaction was stirred at room temperature for 2 hr. The residue was filtered and without more purification to get the product. To the product was dissolved in ethanol (20 ml) and added 2,3-dichloro-1,4-naphthoquinone (0.42 g, 1.85 mmol). The reaction mixture was refluxed for 0.5 h. The residue was purified by flash column over silica gel (ethyl acetate:n-Hexane=1:3, Rf=0.25) to afford 84 (0.15 g, 25.12%) as a red solid. $^1$H NMR (300 MHz, d-Acetone): δ 6.49 (s, 1H), 6.98 (d, J=8.4 Hz, 1H), 7.29 (s, 1H), 7.36 (t, J=3.0 Hz, 1H), 7.53 (d, J=8.1 Hz, 1H), 7.79-7.92 (m, 2H), 8.10-8.20 (m, 2H), 8.58 (s, 1H), 10.31 (s, 1H).

Example 107 2-((1H-indol-5-yl)amino)-3-chloronaphthalene-1,4-dione (85)

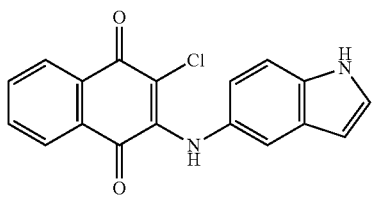 [SMILES: O=C1C(Cl)=C(Nc2ccc3[nH]ccc3c2)C(=O)c2ccccc21]

A mixture of 5-nitroindole (0.50 g, 3.08 mmol) was dissolved in ethanol (10 ml) and added the 10% Pd/C as catalyst. The reaction was stirred at room temperature for 3 hr. The residue was filtered and without more purification to get the product. To the product was dissolved in ethanol (10 ml) and added 2,3-dichloro-1,4-naphthoquinone (0.50 g, 2.20 mmol). The reaction mixture was refluxed for 1 h. The residue was purified by flash column over silica gel (ethyl acetate:n-Hexane=1:3, Rf=0.28) to afford 85 (0.15 g, 21.13%) as a red solid. $^1$H NMR (300 MHz, CDCl$_3$): δ 6.55-6.57 (m, 1H), 7.02 (dd, J=2.1, 8.7 Hz, 1H), 7.29 (t, J=3.0 Hz, 1H), 7.37 (d, J=8.7 Hz, 1H), 7.41-7.42 (m, 1H), 7.66-7.72 (m, 1H), 7.75-7.81 (m, 1H), 7.86 (s, 1H), 8.14 (d, J=6.3 Hz, 1H), 8.21 (d, J=6.6 Hz, 1H), 8.26 (s, 1H).

Example 108 2-chloro-3-((1-((4-methoxyphenyl)sulfonyl)indolin-5-yl)amino)naphthalene-1,4-dione (86)

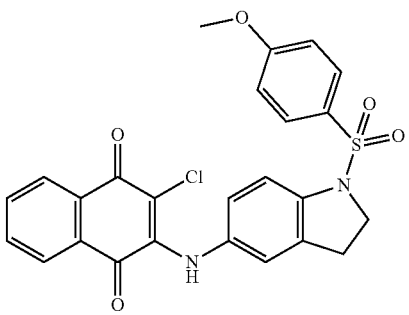 [SMILES: COc1ccc(S(=O)(=O)N2CCc3cc(NC4=C(Cl)C(=O)c5ccccc5C4=O)ccc32)cc1]

A mixture of 5-nitroindole (0.50 g, 3.08 mmol) was dissolved in DMF (3 mL) and added NaH (0.15 g, 3.75 mmol) then stirred for a while, to which was then added 4-methoxybenzenesulfonyl chloride (0.64 g, 3.08 mmol) and stirred for 0.5 hr. The residue was quenched with water and extracted by dichloromethane (30 ml*3). The residue was purified by flash column over silica gel (ethyl acetate:n-hexane=1:3, Rf=0.31) to get the white product. Then the white product (0.16 g, 0.48 mmol) was dissolved in MeOH (10 ml) and stirred under H$_2$ for 1 h. The residue was without further purification and dissolved in EtOH (15 ml). To the reaction mixture was added 2,3-dichloro-1,4-naphthaquinone (0.06 g, 0.26 mmol) and stirred and refluxed for 1 hr. The residue was filtered and purified by flash column over silica gel (ethyl acetate:n-hexane=1:2, Rf=0.08) to afford 86 (0.46 g, 50.46%) as a red solid. $^1$H-NMR (300 MHz, CDCl$_3$): δ 2.86 (t, J=8.7 Hz, 2H), 3.85 (s, 3H), 3.96 (t, J=8.4 Hz, 2H), 6.83 (d, J=8.7 Hz, 2H), 6.92 (d, J=9.0 Hz, 2H), 6.96 (d, J=8.4 Hz, 1H), 7.14 (d, J=8.7 Hz, 1H), 7.63 (d, J=8.4 Hz, 1H), 7.72 (d, J=9.0 Hz, 2H), 7.76-7.81 (m, 1H), 8.13 (d, J=6.6 Hz, 1H), 8.20 (d, J=7.2 Hz, 1H).

Example 109 2-chloro-3-((1-((4-methoxyphenyl)sulfonyl)indolin-7-yl)amino)naphthalene-1,4-dione (87)

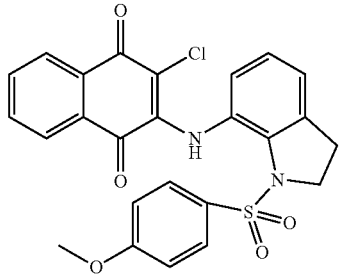 [SMILES: COc1ccc(S(=O)(=O)N2CCc3cccc(NC4=C(Cl)C(=O)c5ccccc5C4=O)c32)cc1]

A mixture of 5-bromo-7-nitroindole (0.50 g, 2.07 mmol), 4-methoxybenzenesulfonyl chloride (0.64 g, 3.11 mmol), and pyridine (3.0 ml) was stirred and refluxed overnight. The residue was purified by flash column over silica gel (ethyl acetate:n-hexane=1:2, Rf=0.35) to get the yellow product. Then the yellow product was dissolved in MeOH (5 ml) and under $H_2$ and 40 psi for overnight. The residue was without further purification to afford as a black solid. A mixture of residue (0.51 g, 1.68 mmol) and 2,3-dichloro-1,4-naphthaquinone (0.40 g, 1.76 mmol) was dissolved in EtOH (15 ml) and stirred and refluxed for 3 day. The residue was filtered and purified by flash column over silica gel (ethyl acetate:n-hexane=1:4, Rf=0.15) to afford 87 (0.46 g, 50.46%) as a red solid. $^1$H-NMR (500 MHz, DMSO-$d_6$): δ 2.22 (t, J=7.5 Hz, 2H), 3.79 (s, 3H), 3.92 (t, J=7.5 Hz, 2H), 6.97 (d, J=7.5 Hz, 1H), 7.00 (d, J=9.0 Hz, 2H), 7.07 (d, J=8.0 Hz, 1H), 7.15 (t, J=8.0 Hz, 1H), 7.46 (d, J=9.0 Hz, 2H), 7.82 (t, J=7.5 Hz, 1H), 7.88 (t, J=8.5 Hz, 1H), 8.04 (m, 2H), 9.38 (s, 1H).

Example 110 2-Chloro-3-(quinolin-8-ylamino)naphthalene-1,4-dione (88)

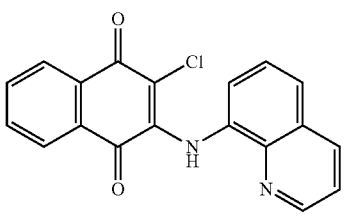 [SMILES: O=C1C(Cl)=C(Nc2cccc3cccnc23)C(=O)c2ccccc21]

A mixture of 2,3-dichloro-1,4-naphthoquinone (0.50 g, 2.2 mmol) and 8-aminoquinoline (0.63 g, 4.40 mmol) was dissolved in ethanol (5 ml). The reaction mixture was refluxed for 16 h. The residue was filtered and washed by dichloromethane, ethyl acetate and methanol. The product was without more purification to afford 88 (0.35 g, 47.52%). $^1$H NMR (300 MHz, CDCl$_3$): δ 7.54 (d, J=7.5 Hz, 1H), 7.64-7.78 (m, 4H), 7.94-7.97 (m, 2H), 8.05 (t, J=9.0 Hz, 2H), 8.86 (d, J=8.7 Hz, 1H), 9.17 (s, 1H).

Example 111 2-chloro-3-(isoindolin-2-yl)naphthalene-1,4-dione (89)

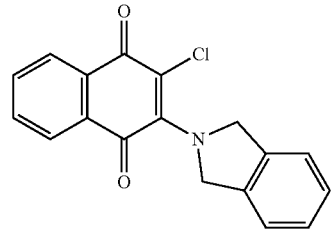 [SMILES: O=C1C(Cl)=C(N2Cc3ccccc3C2)C(=O)c2ccccc21]

A mixture of 2,3-dichloro-1,4-naphthoquinone (0.34 g, 1.50 mmol) and isoindoline (0.30 g, 2.52 mmol) was dissolved in ethanol (10 ml). The reaction mixture was refluxed for overnight. The residue was filtered and without more purification to afford 89 (0.23 g, 49.50%) as a red solid. $^1$H NMR (500 MHz, DMSO-$d_6$): 7.28-7.31 (m, 2H), 7.37-7.40 (m, 2H), 7.71-7.74 (m, 1H), 7.77-7.80 (m, 1H), 7.86 (d, J=7.5 Hz, 1H), 7.93 (d, J=7.5 Hz, 1H).

Example 112 N-(3-chloro-1,4-dioxo-1,4-dihydronaphthalen-2-yl)-4-methoxybenzamide (90)

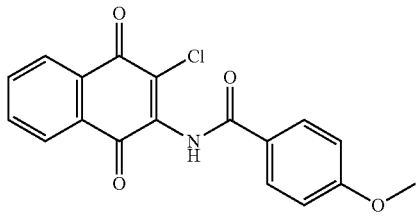 [SMILES: COc1ccc(C(=O)NC2=C(Cl)C(=O)c3ccccc3C2=O)cc1]

A mixture of p-anisoyl chloride (0.49 ml, 3.61 mmol) was added slowly to the corresponding 2-amino-3-chloro-1,4-naphthoquinone (0.50 g, 2.4 mmole) and NaH (0.15 g, 3.61 mmol) in DMF (3 ml) at 0° C. The reaction mixture was warmed to room temperature, and stirring was continued for another 1 h. The residue was purified by flash column over silica gel (EtOAc:n-hexane=1:2) to afford 90 (0.04 g, 4.88%) as a red solid. $^1$H NMR (300 MHz, DMSO-$d_6$): δ 3.84 (s, 3H), 7.08 (d, J=9.0 Hz, 2H), 7.89-7.92 (m, 2H), 7.99 (d, J=8.7 Hz, 2H), 8.03-8.05 (m, 1H), 8.06-8.12 (m, 1H), 10.27 (s, 1H).

Example 113 2-chloro-3-((4-(4-methylpiperazin-1-yl)benzyl)amino)naphthalene-1,4-dione (91)

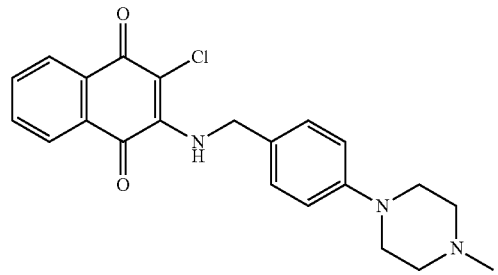 [SMILES: CN1CCN(c2ccc(CNC3=C(Cl)C(=O)c4ccccc4C3=O)cc2)CC1]

A mixture of 4-(4-methylpiperazin-1-yl)benzaldehyde (1.0 g, 4.90 mmol), t-butylcarbamate (1.72 g, 14.69 mmol), triethylsilane (1.56 ml, 9.79 mmol) was dissolved in acetonitrile (21 ml) and TFA (0.75 ml). The reaction mixture was stirred at room temperature under N₂ for overnight. The mixture was washed with saturated NaHCO₃ (aq.) and saturated NaCl (aq.) and worked up. To the residue, TFA (3.1 ml) was added and the stirred for 2 hr. The reaction was quenched with saturated NaHCO₃ (aq.) and an extraction was conducted with dichloromethane. The residue was dissolved in ethanol (10 ml) and to which 2,3-dichloro-1,4-naphthoquinone (0.82 g, 3.60 mmol) were added, and the mixture was refluxed for overnight. The reaction was purified by flash column over silica gel (dichloromethane:methanol=30:1) to afford 91 (0.10 g, 5.16%) as a purple solid. ¹H NMR (300 MHz, CDCl₃): δ 2.36 (s, 3H), 2.59 (t, J=5.1 Hz, 4H), 3.24 (t, J=5.4 Hz, 4H), 4.97 (d, J=6.0 Hz, 2H), 6.13 (brs, 1H), 6.94 (d, J=8.7 Hz, 2H), 7.25 (d, J=8.7 Hz, 2H), 7.63 (t, J=7.5 Hz, 1H), 7.74 (t, J=7.5 Hz, 1H), 8.04 (d, J=7.5 Hz, 1H), 8.17 (d, J=7.5 Hz, 1H).

Example 114 2-chloro-3-((4-(4-ethylpiperazin-1-yl)benzyl)amino)naphthalene-1,4-dione (92)

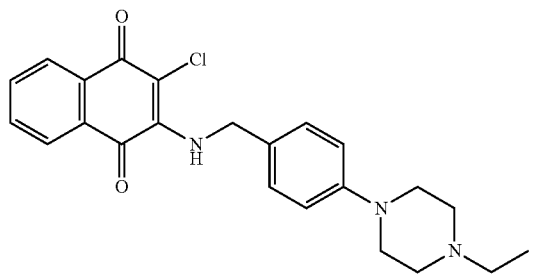 [SMILES: CCN1CCN(c2ccc(CNC3=C(Cl)C(=O)c4ccccc4C3=O)cc2)CC1]

A mixture of 4-(4-ethylpiperazin-1-yl)benzaldehyde (1.50 g, 6.87 mmol), t-butylcarbamate (2.41 g, 20.61 mmol), triethylsilane (2.2 ml, 13.74 mmol) was dissolved in acetonitrile (29.3 ml) and TFA (1.05 ml). The reaction mixture was stirred at room temperature under N₂ overnight. The mixture was washed with saturated (aq.) and saturated NaCl (aq.) and worked up. To the residue, TFA (4.4 ml) was added and the stirred for 2 hr. The reaction was quenched with saturated NaHCO₃ (aq.) and an extraction was conducted with dichloromethane. The residue was dissolved in ethanol (10 ml) and to which 2,3-dichloro-1,4-naphthoquinone (0.95 g, 4.20 mmol) were added, and the mixture was refluxed overnight. The reaction was purified by flash column over silica gel (dichloromethane:methanol=30: 1) to afford 92 (0.08 g, 2.84%) as a purple solid. ¹H NMR (300 MHz, CDCl₃): δ 1.13 (t, J=4.5 Hz, 3H), 2.47 (q, J=4.5 Hz, 2H), 2.60 (t, J=3.0 Hz, 4H), 3.23 (t, J=3.0 Hz, 4H), 4.95 (d, J=3.6 Hz, 2H), 6.13 (brs, 1H), 6.92 (d, J=5.1 Hz, 2H), 7.22 (d, J=5.1 Hz, 2H), 7.61 (t, J=5.1 Hz, 1H), 7.72 (t, J=5.4 Hz, 1H), 8.02 (d, J=4.8 Hz, 1H), 8.15 (d, J=4.8 Hz, 1H).

We claim:
1. A method for providing therapeutic treatment to a neoplastic disease, an inflammatory disorder, an autoimmune disorder, a neurodegenerative disease or a metabolic disorder-comprising contacting a cell with an effective amount of the following compound or administering an effective amount of the following compound or a pharmaceutical composition comprising the following compound and a pharmaceutically acceptable carrier to a subject in need thereof;

wherein the compound having the structure of:

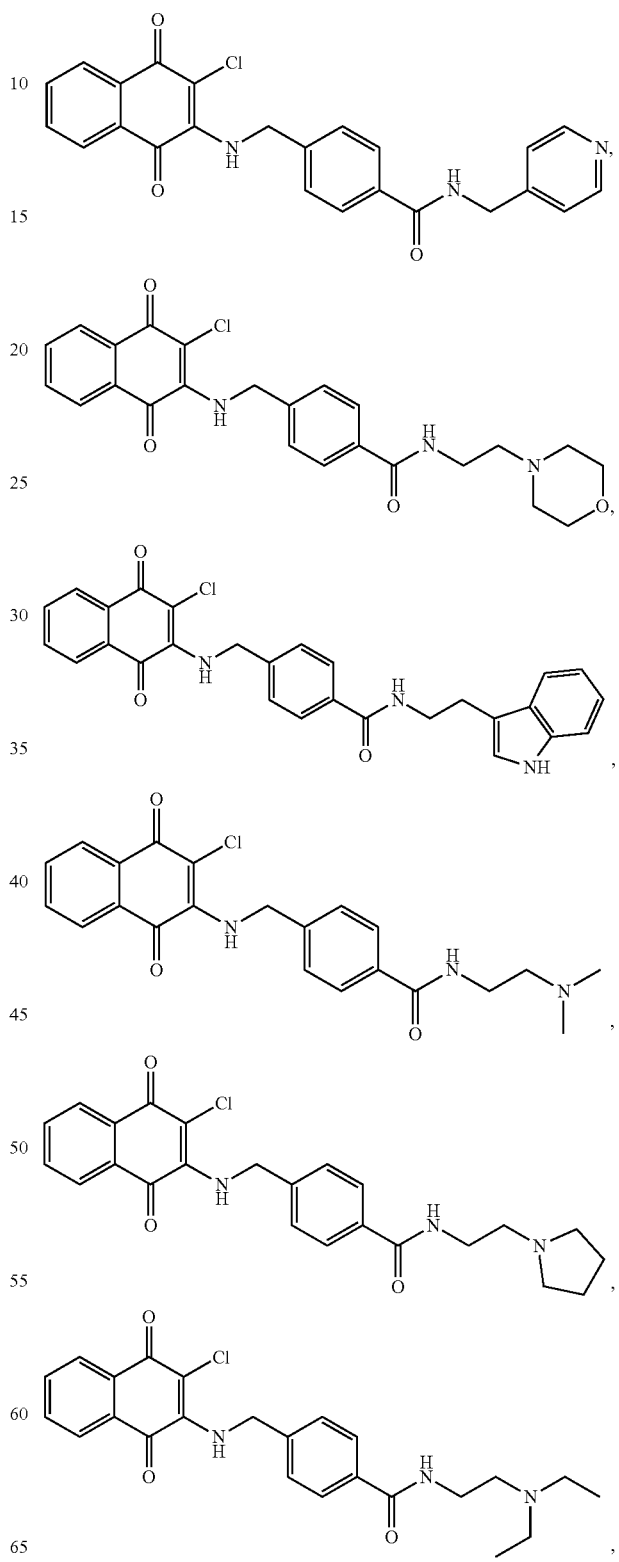

-continued

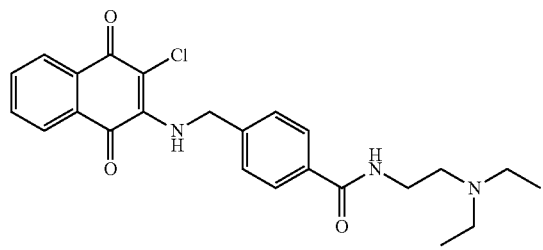

, or

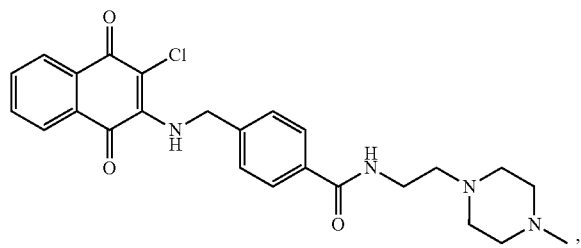

or a tautomer or stereoisomer thereof, or a solvate, prodrug or a pharmaceutically acceptable salt thereof.

2. The method of claim 1, wherein the compound is selected from the group consisting of:

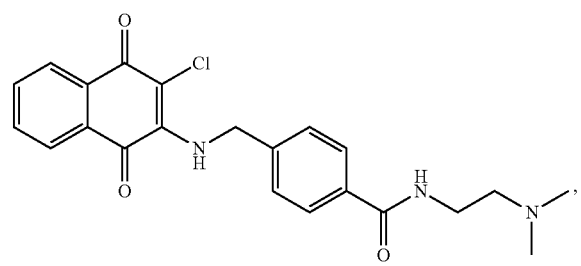

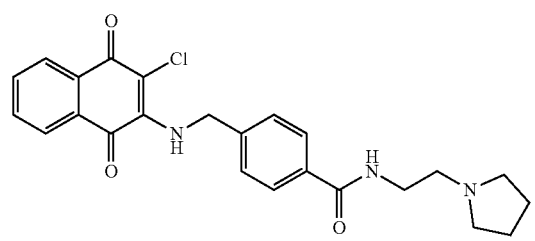

and

-continued

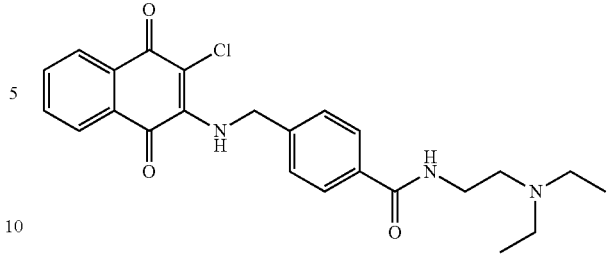

or a tautomer or stereoisomer thereof, or a solvate, prodrug or a pharmaceutically acceptable salt thereof.

3. The method of claim 1, wherein the inflammatory disorder or autoimmune disorder is restenosis, inflammation, rheumatoid arthritis, tissue injury due to inflammation, hyperproliferative diseases, severe or arthritic psoriasis, muscle-wasting diseases, chronic infectious diseases, abnormal immune response, conditions involving vulnerable plaques, injuries related to ischemic conditions, and viral infection or proliferation.

4. The method of claim 1, wherein the compound is administered in combination with a second therapeutic agent.

5. The method of claim 4, wherein the second therapeutic agent is selected from a mitotic inhibitor, vinca alkaloids and vepesid; an anthracycline antibiotic; a nucleoside analog; an EGFR inhibitor; a folate antimetabolite; cisplatin, carboplatin; or a HDAC inhibitor.

6. The method of claim 5, wherein the second therapeutic agent is a corticosteroid, a lubricant, a keratolytic agent, a vitamin $D_3$ derivative, PUVA and anthralin, $\beta_2$-agonist, a corticosteroid, immunosuppressant, NSAID, COX-2 inhibitor, biologic, non-steroidal calcineurin inhibitor, steroidal anti-inflammatory agent, 5-amino salicylic acid, DMARDs, hydroxychloroquine sulfate, inflammatory modulator, agents that interfere with B cell action or penicillamine.

7. The method of claim 5, wherein the mitotic inhibitor is a taxane; optionally, the taxane is paclitaxel or docetaxel.

8. The method of claim 5, wherein the vinca alkaloid is selected from vinblastine, vincristine, vindesine and vinorelbine.

9. The method of claim 5, wherein the anthracycline antibiotic is selected from doxorubicin, daunorubicin, epirubicin, idarubicin, valrubicin and mitoxantrone.

10. The method of claim 5, wherein the nucleoside analog is gemcitabine.

11. The method of claim 5, wherein the EGFR inhibitor is gefitinib or erlotinib.

12. The method of claim 5, wherein the folate antimetabolite is selected from trimethoprim, pyrimethamine and pemetrexed.

* * * * *